United States Patent [19]

Hashimoto et al.

[11] 4,339,449
[45] Jul. 13, 1982

[54] ANALOGOUS COMPOUNDS OF CEPHALOSPORINS, AND PHARMACEUTICAL COMPOSITION COMPRISING THE SAME

[75] Inventors: Masashi Hashimoto, Takarazuka; Matsuhiko Aratani, Suita, both of Japan

[73] Assignee: Fujisawa Pharmaceutical Company, Limited, Osaka, Japan

[21] Appl. No.: 128,507

[22] Filed: Mar. 10, 1980

[30] Foreign Application Priority Data

Mar. 27, 1979 [GB] United Kingdom ............... 7910719

[51] Int. Cl.³ .................... C07D 513/04; A61K 31/54
[52] U.S. Cl. ........................................ 424/246; 544/10
[58] Field of Search .......................... 424/246; 544/10

[56] References Cited

FOREIGN PATENT DOCUMENTS 865632 10/1978 Belgium .

*Primary Examiner*—John M. Ford
*Attorney, Agent, or Firm*—Oblon, Fisher, Spivak, McClelland & Maier

[57] ABSTRACT

A compound of high antimicrobial activity of the formula:

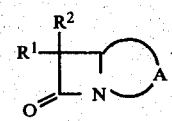

in which
  $R^1$ is amino or a substituted amino group and
  $R^2$ is hydrogen or lower alkoxy, or
  $R^1$ and $R^2$ are combined together to form a group of the formula:

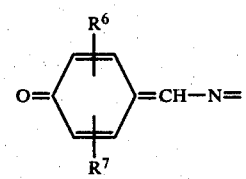

wherein
$R^6$ and $R^7$ are each hydrogen or lower alkyl, and
A is a group of the formula:

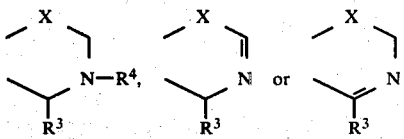

wherein
X is —S— or

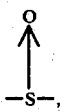

$R^3$ is carboxy or a protected carboxy group and
$R^4$ is hydrogen, hydroxy, or acyl,
and pharmaceutically acceptable salts thereof.

12 Claims, No Drawings

ANALOGOUS COMPOUNDS OF CEPHALOSPORINS, AND PHARMACEUTICAL COMPOSITION COMPRISING THE SAME

The present invention relates to novel analogous compounds of cephalosporins and pharmaceutically acceptable salts thereof. More particularly, it relates to novel analogous compounds of cephalosporins and pharmaceutically acceptable salts thereof, which have anti-microbial activities against pathogenic microorganisms, especially fungus, to processes for the preparation thereof, to pharmaceutical composition comprising the same, and to a method of using the same therapeutically for the treatment of infectious diseases caused by pathogenic microorganisms, especially fungus in human being and animals.

Accordingly, one object of the present invention is to provide novel analogous compounds of cephalosporins and pharmaceutically acceptable salts thereof, which are highly active against pathogenic microorganisms, especially fungus.

Another object of the present invention is to provide processes for the preparation of novel analogous compounds of cephalosporins and salts thereof.

A further object of the present invention is to provide pharmaceutical composition comprising, as active ingredients, said analogous compounds of cephalosporins and pharmaceutically acceptable salts thereof.

Still further object of the present invention is to provide a method for the treatment of infectious diseases caused by pathogenic microorganisms, especially fungus, in human being and animals.

The object analogous compounds of cephalosporins are novel and comprises a new and unique chemical structure, which is characterized by having a nitrogen atom instead of the carbon atom at the 3rd position of the cephalosporin nucleus and have not been expected to any persons skilled in the art, and can be represented by the following general formula:

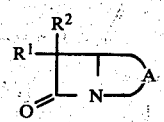
(I)

in which
$R^1$ is amino or a substituted amino group and
$R^2$ is hydrogen or lower alkoxy, or
$R^1$ and $R^2$ are combined together to form a group of the formula:

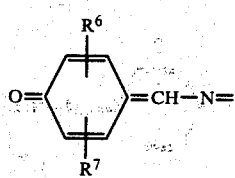

wherein
$R^6$ and $R^7$ are each hydrogen or lower alkyl, and
A is a group of the formula:

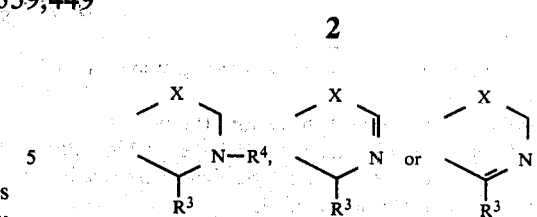

wherein
X is —S— or

$R^3$ is carboxy or a protected carboxy group and
$R^4$ is hydrogen, hydroxy or acyl, and
pharmaceutically acceptable salt thereof.

In the object compounds (I) and the corresponding starting compounds (II), it is to be understood that there may be one or more stereoisomeric pair(s) due to asymmetric carbon atom(s) in those molecules, and these isomers are also included within the scope of the present invention.

As to the object compound, in all of the present specification, it is to be noted that the basic chemical structures thereof are represented by the following formulae, to which there are given nomenclature as shown below.

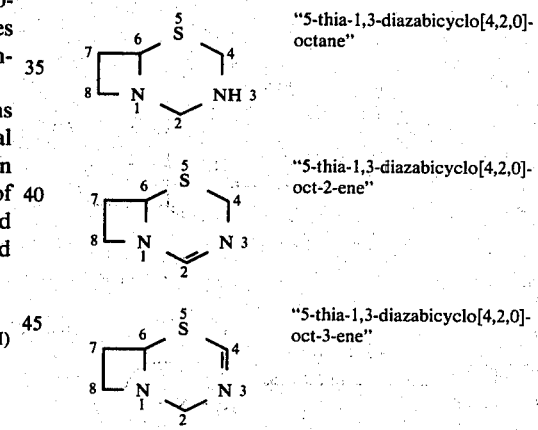

Suitable pharmaceutically acceptable salts of the object compounds (I) including compounds (I-1) to (I-20) mentioned below are conventional non-toxic salts and may include an inorganic base salt, for example, a metal salt such as an alkali metal salt (e.g. sodium salt, potassium salt, etc.) and an alkaline earth metal salt (e.g. calcium salt, magnesium salt, etc.) and an ammonium salt etc.; an organic base salt, for example, an organic amine salt (e.g., trimethylamine salt, triethylamine salt, pyridine salt, picoline salt, dicyclohexylamine salt, N,N'-dibenzylethylenediamine salt, N-methylglucamine salt, diethanolamine salt, triethanolamine salt, tris(hydroxymethylamino)methane salt, etc.) etc.; an organic carboxylic or sulfonic acid addition salt (e.g., formate, acetate, maleate, tartrate, methanesulfonate, benzenesulfonate, toluenesulfonate, etc.); an inorganic acid addition salt (e.g., hydrochloride, hydrobromide, sulfate, phosphate, etc.); a salt with a basic or acidic amino acid (e.g., arginine, aspartic acid, glutamic acid, etc.), and the like.

According to the present invention, the object compounds (I) and the pharmaceutically acceptable salts thereof can be prepared by the processes as illustrated by the following reaction schemes.

Process 1:

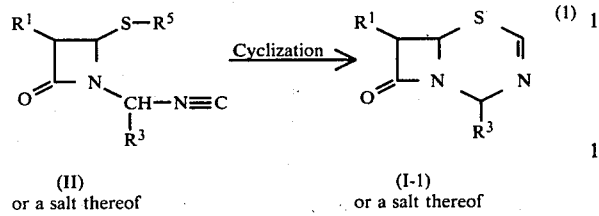

(II) or a salt thereof → (I-1) or a salt thereof

Process 2:

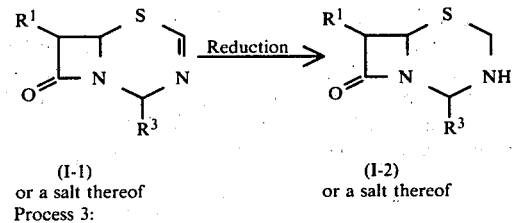

(I-1) or a salt thereof → (I-2) or a salt thereof

Process 3:

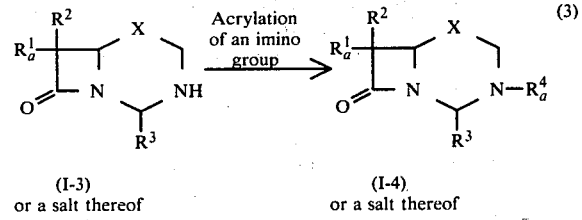

(I-3) or a salt thereof → (I-4) or a salt thereof

Process 4:

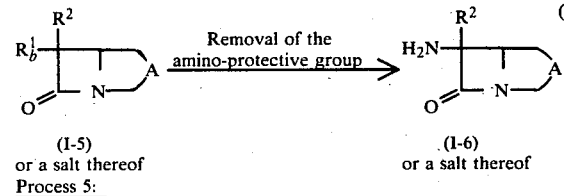

(I-5) or a salt thereof → (I-6) or a salt thereof

Process 5:

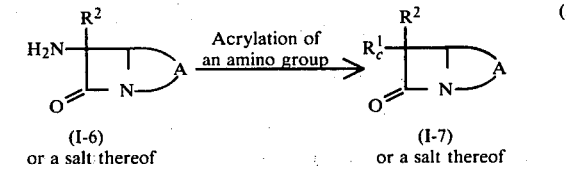

(I-6) or a salt thereof → (I-7) or a salt thereof

Process 6:

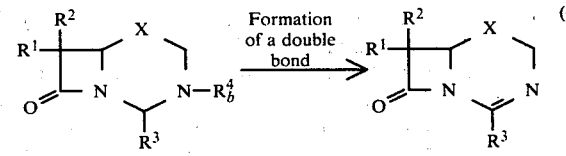

(I-8) or a salt thereof → (I-9) or a salt thereof

Process 7:

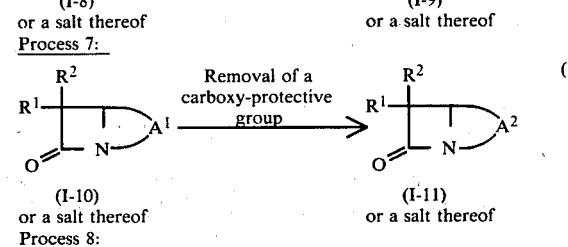

(I-10) or a salt thereof → (I-11) or a salt thereof

Process 8:

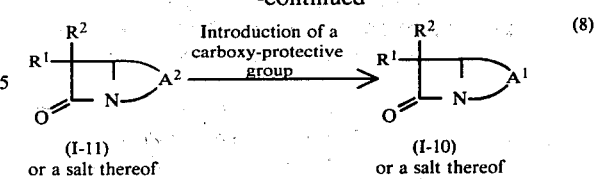

(I-11) or a salt thereof → (I-10) or a salt thereof

Process 9:

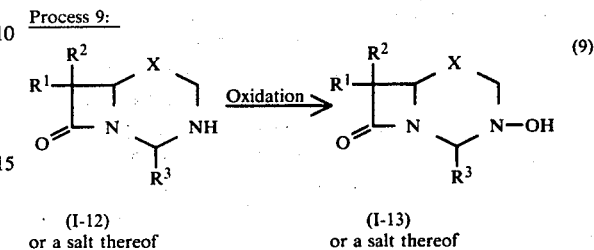

(I-12) or a salt thereof → (I-13) or a salt thereof

Process 10:

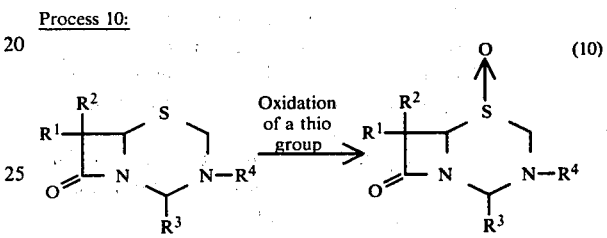

(I-14) or a salt thereof → (I-15) or a salt thereof

Process 11:

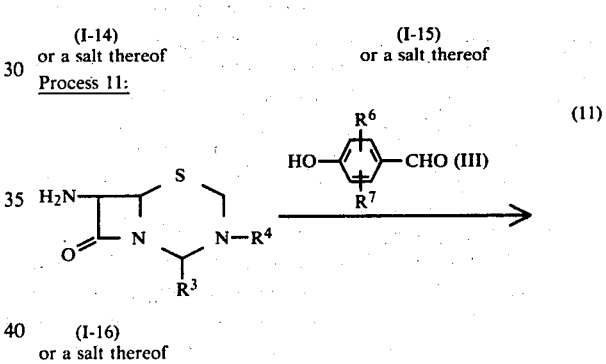

(I-16) or a salt thereof

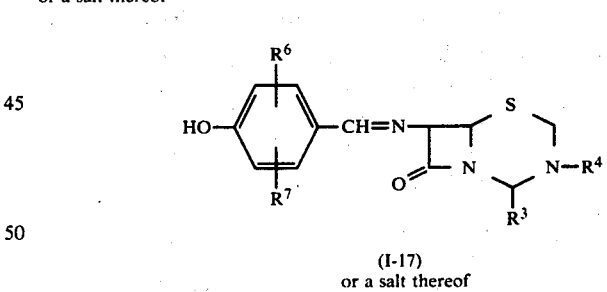

(I-17) or a salt thereof

↓ Oxidation

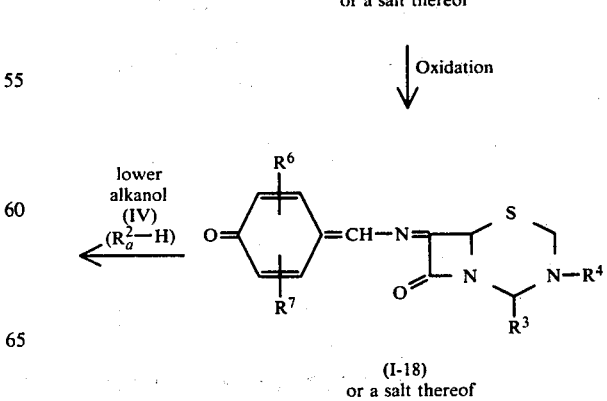

(I-18) or a salt thereof

-continued

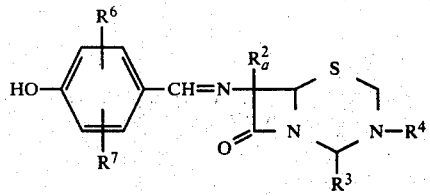

(I-19)
or a salt thereof

↓ Base

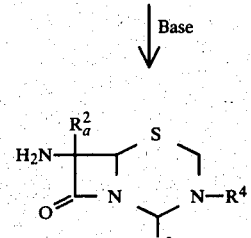

(I-20)
or a salt thereof in which
$R^1$, $R^2$, $R^3$, $R^4$, $R^6$, $R^7$, X and A are each as defined above;
$R_a^1$ is a substituted amino group;
$R_b^1$ is a protected amino group;
$R_c^1$ is acylamino;
$R_a^2$ is lower alkoxy;
$R_a^4$ is acyl;
$R_b^4$ is mono(or di or tri)-halo(lower)alkanesulfonyl;
$R^5$ is a mercapto-protective group;
$A^1$ is a group of the formula:

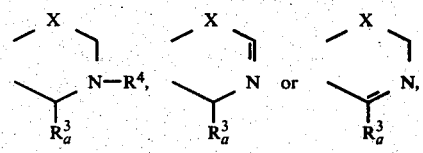

wherein
$R_a^3$ is a protected carboxy group and
$R^4$ and X are each as defined above; and
$A^2$ is a group of the formula:

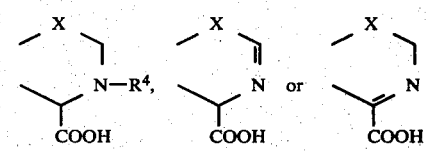

wherein $R^4$ and X are each as defined above.

Some of the starting compound (II) in Process 1 are novel and can be, for example, prepared from known compounds (II-a) and (II-b) by the method in the following reaction schemes or a similar manner thereto.

Preparation A:

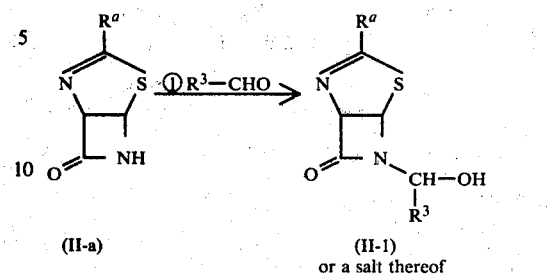

(II-a)      (II-1)
              or a salt thereof

↓ ② Halogenation

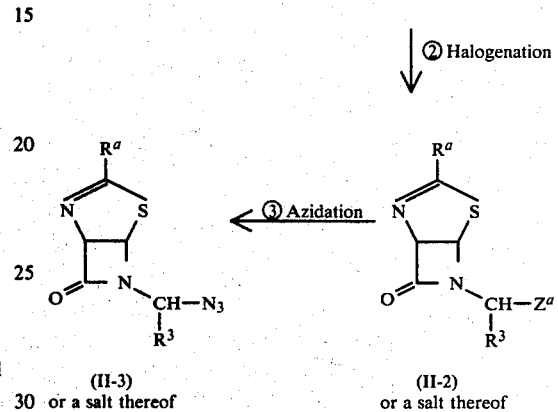

(II-3)      (II-2)
or a salt thereof      or a salt thereof

↓ ④ Silver salt of an acid

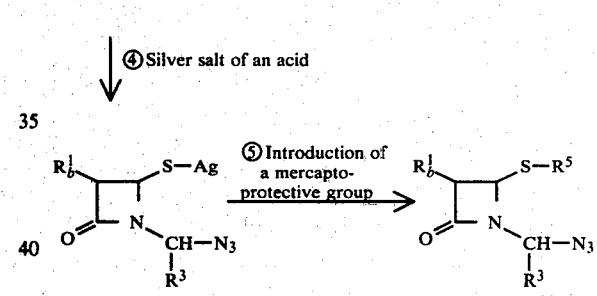

(II-4)      (II-5)
or a salt thereof      or a salt thereof in which
$R_b^1$, $R^3$ and $R^5$ are each as defined above,
$R^a$ is a residue excluded a radical —"CONH—" from the acylamino group for $R_b^1$, and $Z^a$ is halogen.

Preparation B:

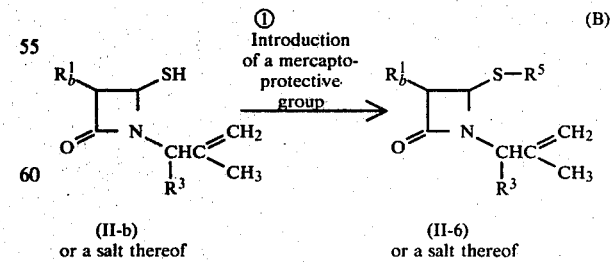

(II-b)      (II-6)
or a salt thereof      or a salt thereof

↓ ② Base

-continued
Preparation B:

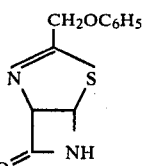

(II-8) or a salt thereof    ③ Ozonolysis    (II-7) or a salt thereof

④ Reduction

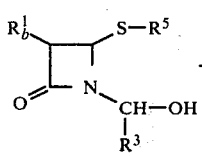

(II-9) or a salt thereof    ⑤ Halogenation    (II-10) or a salt thereof

⑥ Azidation

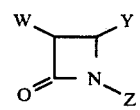

(II-5) or a salt thereof in which $R_b^1$, $R^3$, $R^5$ and $Z^a$ are each as defined above.

Preparation C:

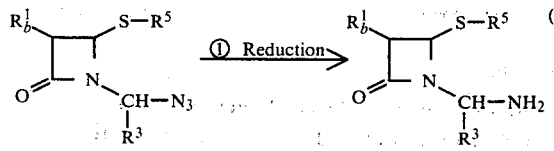

(II-5) or a salt thereof    ① Reduction    (II-11) or a salt thereof

② Formylation

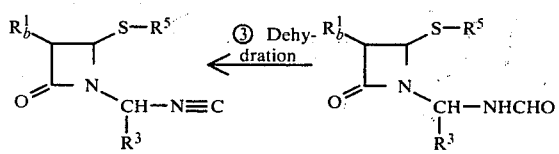

(II) or a salt thereof    ③ Dehydration    (II-12) or a salt thereof in which $R_b^1$, $R^3$ and $R^5$ are each as defined above.

In the above Preparations A and B, the starting compounds (II-a) and (II-b) are known and representative examples thereof are described in the literatures as shown below.

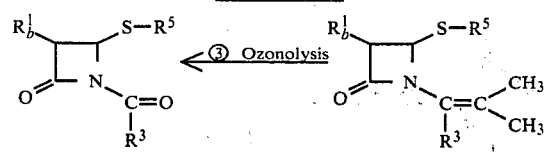

Journal of the American Chemical Society, Volume 94, Page 1021

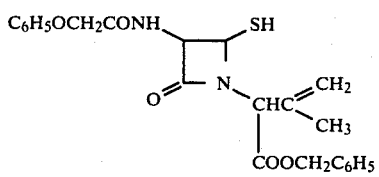

Journal of the Chemical Society, Chemical Communication, 1978, Page 239

Preferred new starting compound of the present invention can be represented by the following general formula:

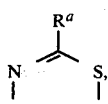

(II)

in which
W is a protected amino group and Y is —S—Ag or —S—$R^5$, wherein $R^5$ is as defined above, or
W and Y are combined together to form a group of the formula:

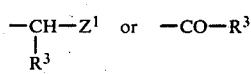

wherein $R^a$ is as defined above, and
Z is a group of the formula:

$$-\underset{\underset{R^3}{|}}{CH}-Z^1 \quad \text{or} \quad -CO-R^3$$

wherein
$R^3$ is as defined above, and
$Z^1$ is azido, hydroxy, amino, formamido, isocyano or halogen,
provided that, when W and Y are combined together to form a group of the formula:

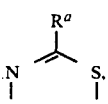

wherein $R^a$ is as defined above, then Z is a group of the formula:

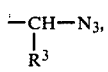

wherein $R^3$ is as defined above, or salts thereof.

Suitable salts of the starting compound (II) including compounds (II′), (II-1) to (II-12) are the same ones as the object compounds (I).

In the above and subsequent description of the present specification, suitable examples and illustration of the various definitions to be included within the scope thereof are explained in detail as follows.

The term "lower" in the present specification is intended to mean a group having 1 to 6 carbon atoms, and the term "higher" is intended to mean a group having 7 to 18 carbon atoms, unless otherwise provided.

Suitable "a substituted amino group" may include acylamino, mono(or di or tri)phenyl(lower)-alkylamino (e.g. benzylamino, benzhydrylamino, tritylamino, etc.), a group of the formula:

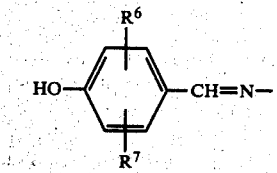

wherein $R^6$ and $R^7$ are each hydrogen or lower alkyl (e.g. methyl, ethyl, propyl, isopropyl, butyl, isobutyl, tert-butyl, pentyl, neopentyl, hexyl, etc.), and the like.

Suitable "acyl" group and "acyl" moiety in the term of "acylamino" may include one which is conventionally used in cephalosporin and penicillin compounds as an acyl group of the amino group at their 7th or 6th position, and suitable acyl may include aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, succinyl, hexanoyl, heptanoyl, stearoyl, etc.);
lower or higher alkoxycarbonyl (e.g. methoxycarbonyl, ethoxycarbonyl, t-butoxycarbonyl, t-pentyloxycarbonyl, heptyloxycarbonyl, etc.);
lower or higher alkanesulfonyl (e.g. methanesulfonyl, ethanesulfonyl, etc.); or the like;

Aromatic acyl such as
aroyl (e.g. benzoyl, toluoyl, naphthoyl, etc.);
ar(lower)alkanoyl such as phenyl(lower)alkanoyl (e.g. phenylacetyl, phenylpropionyl, etc.);
aryloxycarbonyl (e.g. phenoxycarbonyl, naphthyloxycarbonyl, etc.);
aryloxy(lower)alkanoyl such as phenoxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.);
heterocyclic(lower)alkanoyl (e.g. thienylacetyl, thiazolylacetyl, tetrazolylacetyl, etc.);
heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered)heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) etc.;

saturated 3 to 8-membered (more preferably 5 or 6-membered)heteromonocyclic group containing 1 to 4 nitrogen atom(s), for example, pyrrolidinyl, imidazolidinyl, piperidino, piperazinyl, etc.:

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.; unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.)etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6 membered) heteromonocyclic group containing 1 to 2 sulfur atom(s), for example, thienyl, dihydrodithiinyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered)heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The acyl moiety thus defined may optionally be substituted by one to ten, same or different, suitable substituent(s) such as:

lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl; cyclohexadienyl, etc.); hydroxy; halogen (e.g. chloro, bromo, etc.); amino; protected amino as mentioned below; cyano; nitro; carboxy; protected carboxy as mentioned below; sulfo; sulfamoyl; imino; oxo; amino(lower)alkyl (e.g. aminomethyl, aminoethyl, etc.); a group of the formula: $=N-OR^8$ wherein $R^8$ is hydrogen, lower alkyl as aforementioned, lower alkenyl (e.g. vinyl, allyl, 2-butenyl, etc.), lower alkynyl (e.g. ethynyl, 2-propynyl, etc.), ar(lower)alkyl such as phenyl(lower)alkyl (e.g. benzyl, phenethyl, etc.), lower alkylthio(lower)alkyl (e.g. methylthiomethyl, methylthioethyl, etc.), carboxy(lower)alkyl (e.g. carboxymethyl, carboxyethyl, etc.) or lower alkyl (e.g. methyl ethyl, etc.) substituted by a protected carboxy as mentioned below.

Preferred examples of "acyl" moiety in the term of "acylamino" for $R^1$, $R_a^1$ and $R_c^1$ may be phenoxy(lower)alkanoyl (e.g. phenoxyacetyl, phenoxypropionyl, phenoxybutyryl, phenoxyvaleryl, phenoxyhexanoyl, etc.) and thienyl(lower)alkanoyl (e.g. thienylacetyl, thienylpropionyl, thienylbutyryl, thienylvaleryl, thienylhexanoyl, etc.) and preferred ones of "acyl" group for $R^4$ and $R_a^4$ may be lower alkanoyl (e.g. formyl, acetyl, propionyl, butyryl, isobutyryl, valeryl, isovaleryl, hexanoyl, etc.) and mono(or di or tri)-halo(lower)alkanesulfonyl (e.g. chloromethanesulfonyl, dichloromethanesulfonyl, trifluoromethanesulfonyl, trifluoroethanesulfonyl, trichloroethanesulfonyl, etc.).

Suitable "mono (or di or tri)-halo(lower)alkanesulfonyl" may include those as aforementioned.

Suitable "an amino-protective group" in the term of "a protected amino group" may include acyl as aforementioned, and preferred one may be phenyl(lower)alkanoyl and phenoxy(lower)alkanoyl.

Suitable "lower" alkoxy may include methoxy, ethoxy propoxy, isopropoxy, buthoxy, pentyloxy, hexyloxy, and the like, and preferred one is $C_1-C_2$ alkyl, and most preferred one is methoxy.

Suitable "a mercapto-protective group" may include acyl as aforementioned, substituted or unsubstituted ar(lower)alkyl such as mono(or di or tri)phenyl(lower)alkyl optionally substituted by nitro (e.g. benzyl, benzhydryl, trityl, 4-nitrobenzyl, etc.) and the like, and preferred acyl may be lower alkanoyl, lower alkoxycarbonyl, mono(or di or tri)-halo(lower)alkoxycarbonyl, more preferred one is tri-halo(lower)alkoxycarbonyl, and most preferred one is 2,2,2-trichloroethoxycarbonyl.

Suitable "a carboxy-protective group" in the term of "a protected carboxy group" may include ester, which is conventionally used in cephalosporin and penicillin compounds as the carboxy-protective group of the carboxy group at their 4th or 3rd position. And suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower cycloalkyl(lower)alkyl ester (e.g. 1-cyclopropylethyl ester, etc.); lower alkenyl ester (e.g., vinyl ester, allyl ester, etc.); lower alkynyl ester (e.g., ethynyl ester, propynyl ester, etc.); lower alkoxy(lower)alkyl ester (e.g., methoxymethyl ester, ethoxymethyl ester, isopropoxymethyl ester, 1-methoxyethyl ester, 1-ethoxyethyl ester, etc.); lower alkylthio(lower)alkyl ester (e.g., methylthiomethyl ester, ethylthiomethyl ester, ethylthioethyl ester, isopropylthiomethyl ester, etc.); mono(or di or tri)-halo(lower)alkyl ester (e.g., 2-iodoethyl ester, 2,2,2-trichloroethyl ester, etc.); lower alkanoyloxy(lower)alkyl ester (e.g., acetoxymethylester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g. mesylmethyl ester, 2-mesylethyl ester etc.); ar(lower)alkyl ester, for example, phenyl(lower)alkyl ester optionally substituted by one or more suitable substituent(s) such as nitro, hydroxy, lower alkoxy or the like (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-t-butylbenzyl ester, etc.); aryl ester optionally substituted by one or more suitable substituent(s) such as alkyl-substituted or unsubstituted phenyl ester optionally substituted by halogen, lower alkoxy or the like (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; and the like.

Preferred examples of "a carboxy-protective group" may be lower alkoxy(lower)alkyl ester, phenyl(lower)alkyl ester optionally substituted by nitro, and lower alkanoyloxy(lower)alkyl ester.

Suitable "lower alkyl" may include methyl, ethyl, propyl, isopropyl, butyl, isobutyl, tert-butyl, pentyl, neopentyl, hexyl, and the like.

The processes for the preparation of the object compounds (I) of the present invention are explained in detail in the following.

(1) Process 1:

The object compound (I-1) or a salt thereof can be prepared by subjecting the compound (II') or a salt thereof to cyclization reaction.

This cyclization reaction can be carried out by removing the mercapto-protective group in the compound (II').

According to this reaction, once the mercapto-protective group in the starting compound (II') is removed, the resulting compound having the free mercapto group cyclized immediately to give the object compound (I-1).

Suitable method for this removal reaction may include reduction, hydrolysis, a method using silver salt, and the like.

In the above methods, suitable reagents to be used are exemplified as follows.

(i) For Hydrolysis:

Hydrolysis is preferably carried out in the presence of an acid.

Suitable acid is an inorganic acid (e.g. hydrochloric acid, hydrobromic acid, sulfuric acid, etc.), an organic acid (e.g. formic acid, acetic acid, trifluoroacetic acid, propionic acid, benzene-sulfonic acid, p-toluenesulfonic acid, etc.), an acidic ion-exchange resin and the like, and among the above acid, preferred one may be weak acid such as acetic acid, and the like.

The hydrolysis is usually carried out in a conventional solvent which does not adversely influence the reaction such as water, methanol, ethanol, propanol, tetrahydrofuran, N,N-dimethylformamide, dioxane or a mixture thereof.

The reaction temperature of this hydrolysis is not critical and the reaction is usually carried out under cooling to at ambient temperature.

(ii) For reduction:

Reduction is carried out in a conventional manner, including chemical reduction and catalytic reduction.

Suitable reducing agents to be used in chemical reduction are a combination of metal (e.g. tin, zinc, iron, etc.), or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.)

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to at ambient temperature.

(iii) For a method using silver salt of an acid:

Suitable silver salt of an acid may include silver fluoroborate, silver perchlorate, and the like.

As to this process, the reaction is preferably carried out in an acidic condition.

(2) Process 2:

The object compound (I-2) or a salt thereof can be prepared by reducing the compound (I-1) or a salt thereof.

The present reduction can be conducted by a conventional method which can reduce a >C=N— group to >CH—NH—group, for example, by using a reducing agent such as aforementioned in Process 1, alkali metal borohydrides (e.g. sodium borohydride, sodium cyanoborohydride, etc.), alminum hyride, diisopropyl alminum hydride, metal amalgam (e.g. alminum amalgam, etc.), borane complex with amines (e.g. tert-butylamine, N,N-dimethylaniline, lutidine, morpholine, N-phenylmorpholine, triethylamine, etc.), borane complex with ethers (e.g. tetrahydrofuran, etc.), diborane, and the like.

The reduction is usually carried out in a conventional solvent which does not adversely influence the reaction such as water, methanol, ethanol, N,N-dimethylformamide, tetrahydrofuran or a mixture thereof.

The reaction temperature of this reduction is not critical and the reaction is usually carried out under cooling to at ambient temperature.

(3) Process 3:

The object compound (I-4) or a salt thereof can be prepared by reacting the compound (I-3) or a salt thereof with an acylating agent.

The acylating agent to be used in this reaction may include an organic carboxylic and sulfonic acid or a reactive derivative thereof.

Suitable reactive derivative of the acylating agent may include, for example, an acid halide, an acid anhydride, an activated amide, an activated ester, and the like, and preferably an acid chloride and acid bromide; a mixed acid anhydride with an acid such as substituted phosphoric acid (e.g., dialkylphosphoric acid, pheylphosphoric acid, diphenylphosphoric acid, dibenzylphosphoric acid, halogenated phosphoric acid, etc.), dialkylphosphorus acid, sulfurous acid, thiosulfuric acid, sulfuric acid, alkyl carbonate (e.g., methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g., benzoic acid, etc.); a symmetrical acid anhydride; an activated acid amide with a heterocyclic compound contained imino function such as imidazole, 4-substituted imidazole, dimethylpyrazole, triazole or tetrazole; an activated ester (e.g., p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H) pyridone, N-hydroxysuccinimide, N-hydroxyphthalimide, 1-hydroxybenzotriazole, 1-hydroxy-6-chlorobenzotriazole, etc.), and the like. The suitable reactive derivative can optionally be selected from the above according to the kind of the compound (I-3) to be used practically.

This acylation reaction is preferably carried out in the presence of an organic or inorganic base such as alkali metal (e.g. lithium, sodium, potassium, etc.), alkaline earth metal (e.g. calcium, magnesium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), trialkylamine (e.g. triethylamine, etc.), pyridine compound (e.g. pyridine, lutidine, picoline, etc.), quinoline, and the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

Among these solvents, hydrophilic solvents may be used in a mixture with water. The reaction can usually be carried out under cooling.

When the acylating agent is used in a form of the free acid or a salt in this reaction, the reaction is preferably carried out in the presence of a condensing agent such as a carbodiimide compound [e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g., N,N'-carbonylbis(2-methylimidazole), pentamethyleneketene-N-cyclohexylimine, diphenylketene-N-cyclohexylimine, etc.); an olefinic or acetylenic ether compounds (e.g., ethoxyacetylene, β-chlorovinylethyl ether), a sulfonic acid ester of N-hydroxybenzotriazole derivative [e.g., 1-(4-chlorobenzenesulfonyloxy)-6-chloro-1H-benzotriazole, etc.], a combination of trialkylphosphite or triphenylphosphine and carbon tetrachloride, disulfide or diazacarboxylate, a phosphorus compound (e.g., ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as dimethylformamide, diethylacetamide, N-methylformamide or the like with a halogen compound such as thionyl chloride, phosphoryl chloride, phosgene or the like.

The reaction temperature is not critical and the reaction is usually carried out under cooling to at ambient temperature.

(4) Process 4:

The object compound (I-6) or a salt thereof can be prepared by subjecting the compound (I-5) or a salt thereof to removal reaction of the amino-protective group.

Suitable method for this removal reaction may include hydrolysis, reduction, a combined method comprising iminohalogenation and iminoetherification, followed by hydrolysis, and the like.

The methods of hydrolysis and reduction, and the reaction conditions (e.g. reaction temperature, solvent, etc.) are substantially the same as those illustrated for the removal reaction of the mercapto-protective group in the compound (II) in Process 1, and therefore are to be referred to said explanation.

As to the combined method, when the protected amino group for $R_b^1$ is an organic carboxamide, the carboxamide bond can be more preferably cleaved by the following modified hydrolysis. That is, the compound (I-5) is first subjected to iminohalogenation, iminoetherification, and then hydrolysis. The first and second steps of this method are preferably carried out in an anhydrous solvent. Suitable solvent for the first step (i.e. iminohalogenation) is an aprotic solvent such as methylene chloride, chloroform, diethyl ether, tetrahydrofuran, dioxane, etc., and for the second step (i.e. iminoetherification) is usually the same as those in the above first step. These two steps and the last step (i.e. hydrolysis step) are most preferably conducted in one-batch system.

Suitable iminohalogenating agents includes a halogenating agent such as phosphorus compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, etc.) or the corresponding alkanol having alkoxy (e.g. 2-methoxyethanol, 2-ethoxyethanol, etc.), and alkoxide of metal such as alkali metal, alkaline earth metal (e.g. sodium methoxide, potassium ethoxide, magnesium ethoxide, lithium methoxide, etc.), and the like. Thus obtained reaction product is, if necessary, hydrolyzed in a conventional manner. The hydrolysis is preferably carried out at ambient temperature or under cooling, and proceeds simply pouring the reaction mixture into water or a hydrophilic solvent such as alcohol (e.g. methanol, ethanol, etc.) moistened or admixed with water, and if necessary, with addition of an acid or base as exemplified in the hydrolysis.

(5) Process 5:

The object compound (I-7) or a salt thereof can be prepared by reacting the compound (I-6) or a salt thereof with an acylating agent.

In this reaction, the starting compound (I-6) can be used in the activated form at the amino group of the 7th position thereof and such activated form may include a conventional one, for example, a silyl derivative formed by the reaction of the compound (I-6) with a silyl compound such as bis(trimethylsilyl)acetamide, trimethylsilylacetamide, etc.; isocyanate, isothiocyanate, etc.; Schiff's base or its tautomeric enamine type isomer formed by the reaction of the amino group with a carbonyl compound such as an aldehyde compound (e.g., acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g., acetone, methyl ethyl ketone, methyl isobutyl ketone, acetylacetone, ethyl acetoacetate, etc.), and the like.

This acylation reaction is substantially the same as those illustrated for the acylation reaction of the compound (I-3) in Process 3, and therefore the reaction conditions (e.g. reaction temperature, solvent, etc.) are to be referred to said explanation.

(6) Process 6:

The object compound (I-9) or a salt thereof can be prepared by subjecting the compound (I-8) or a salt thereof to a formation reaction of the C=N bond.

This reaction is carried out in the presence of a base.

The base to be used in this reaction may include an inorganic base such as alkali metal hydride (e.g. sodium hydride, potassium hydride, etc.), alkaline earth metal hydride (e.g. calcium hydride, etc.), an organic base such as trialkylamine (e.g. triethylamine, diisopropylethyl-amine, etc.), diazabicyclo compound (e.g. 1,5-diazabicyclo[3,4,0]non-5-ene, 1,5-diazabicyclo[5,4,0]undec-5-ene, 1,4-diazabicyclo[2,2,2]octane, etc.), metal triphenylmethide such as alkali metal triphenylmethide (e.g. sodium triphenylmethide, lithium triphenylmethide, potassium triphenylmethide, etc.), lithium dialkyl or alkyl cycloalkylamide (e.g. lithium diisopropylamide, lithium isopropyl cyclohexylamide, etc.), and the like.

This reaction is preferably carried out under anhydrous condition in a solvent which does not adversely influence the reaction such as methylene chloride, chloroform, carbon tetrachloride, tetrahydrofuran, or a mixture thereof.

The reaction temperature is not critical and the reaction is usually carried out under cooling to at ambient temperature.

(7) Process 7:

The object compound (I-11) or a salt thereof can be prepared by subjecting the compound (I-10) or a salt thereof to removal, reaction of the carboxy-protective group.

The reaction is carried out by a conventional method such as hydroylsis, reduction, a method using Lewis acid or the like.

The methods of hydrolysis and reduction, and the reaction conditions (e.g. reaction temperature, solvent, etc.) are substantially the same as those illustrated for the removal reaction of the mercapto-protective group of the compound (II) in Process 1, and therefore are to be referred to said explanation.

The method using Lewis acid is preferable to eliminate substituted or unsubstituted ar(lower)alkyl ester and carried out by reacting the compound (I-10) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), or the like.

This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof. The reaction temperature is not critical, and the reaction is usually carried out under cooling, at ambient temperature or under warming.

(8) Process 8:

The object compound (I-10) or a salt thereof can be prepared by introducing a carboxy-protective group into the compound (I-11) or a salt thereof.

An introducing agent of a carboxy-protective group to be used in this reaction may include a conventional esterifying agent such as an alcohol or its reactive equivalent (e.g. halide, sulfonate, sulfate, diazo compound, etc.) or the like.

This reaction is usually carried out in the presence of a base as aforementioned in Process 3, in a conventional solvent which does not adversely influence the reaction such as N,N-dimethylformamide, tetrahydrofuran or a mixture thereof.

The reaction temperature is not critical and the reaction is carried out under cooling to at ambient temperature.

(9) Process 9:

The object compound (I-13) or a salt thereof can be prepared by oxidizing the compound (I-12) or a salt thereof.

The oxidizing agent to be used in this reaction may include conventional one which can oxidize an amino group to hydroxyamino group such as cupric compound (e.g. cupric sulfate, cupric chloride, etc.), ferric compound (e.g. ferric chloride, potassium ferricyanide, etc.), benzoquinone compound (e.g. tetrachloro-1,4-benzoquinone, tetrachloro-1,2-benzoquinone, 2,3-dichloro-5,6-dicyano-1,4-benzoquinone, etc.), combination of copper compound such as the above cupric compound and cuprous compound (e.g. cuprous chloride, etc.) and oxygen, and the like.

This reaction is usually carried out in a conventional solvent which does not adversely influence the reaction such as water, acetic acid, benzene, or a mixture thereof, and the like.

The reaction temperature is not critical and the reaction is carried out at ambient temperature.

(10) Process 10:

The object compound (I-15) or a salt thereof can be prepared by oxidizing the compound (I-14) or a salt thereof.

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt thereof, etc.), ozone, hydrogen peroxide, urea-hydrogen peroxide, N-halosuccinimide (e.g. N-bromosuccinimide, N-chlorosuccinimide, etc.), hypochlorite compound (e.g. tert-butyl hypochlorite, etc.), permanganate (e.g. potassium permanganate, etc.), or any other conventional oxidizing agent which can oxidize a thio group to a sulfinyl group.

The present reaction can also be carried out in the presence of a compound comprising Group Vb or VI b metal in the Periodic Table of elements, for example, tungstic acid, molybdic acid, vanadic acid, etc., or an alkali or an alkaline earth metal salt thereof.

The present oxidation reaction is usually carried out in a conventional solvent which does not adversely influence the reaction such as water, acetic acid, chloroform, methylene chloride, acetone, methanol, ethanol or a mixture thereof.

The reaction temperature is not critical and the reaction is preferably carried out under cooling to at ambient temperature.

(11) Process 11:

The object compound (I-20) or a salt thereof can be prepared by reacting the compound (I-16) or a salt thereof with benzaldehyde compound (III) (the first step), by oxidizing the resultant compound (I-17) (the second step), by reacting the resultant compound (I-18) with lower alkanol (IV) (the third step) and then by reacting the resultant compound (I-19) with a base (the final step).

(i) The first step:

In the first step, in case that the salt of the compound (I-16) are used as the starting compound, it may be previously transformed into its free amino compound in the presence of a conventional base such as an alkali metal carbonate (e.g. sodium carbonate, potassium carbonate, etc.), alkali metal bicarbonate (e.g. sodium bicarbonate, potassium bicarbonate, etc.), alkaline earth metal carbonate (e.g. calcium carbonate, magnesium carbonate, etc.), mono- or di-alkali metal phosphate (e.g. potassium dihydrogenphosphate, dipotassium hydrogenphosphate, etc.), or the like.

The present reaction is usually carried out in a solvent such as methylene chloride, carbon tetrachloride, benzene, toluene, xylene, methanol, ethanol, diethyl ether, dioxane, or any other solvent which does not adversely influence the reaction, or a mixture thereof.

The reaction is preferably carried out by removing water formed in the course of the reaction.

The reaction temperature is not critical and the reaction is usually carried out under warming or heating.

Thus obtained compound (I-17) can also be used as it is for the starting compound of the second step without isolation.

(ii) The second step:

The oxidizing agent to be used in this second step may include one which can oxidize a 4-hydroxyphenyl group to a 4-oxo-2,5-cyclohexadienyl-1-idene group such as nickel peroxide, lead dioxide, manganese dioxide, benzoquinone, and preferred one is nickel peroxide.

The present reaction is preferably carried out under anhydrous condition and is usually carried out in a solvent such as methylene chloride, carbon tetrachloride or any other solvent which does not adversely influence the reaction or a mixture thereof.

The reaction temperature is not critical and the reaction is usually carried out under cooling to at ambient temperature.

Thus obtained compound (I-18) or a salt thereof is preferably used as it is for the starting compound of the third step without any isolation.

(iii) The third step:

The lower alkanol of the formula (IV): $R_a{}^2$—H, wherein $R_a{}^2$ is as defined above, to be used in this step is a conventional one such as methanol, ethanol, propanol, isopropanol, butanol, pentanol, hexanol, and the like.

The reaction temperature is not critical and the reaction is usually carried out at ambient temperature.

The obtained compound (I-19) or a salt thereof can be used as it is for the following final step without isolation.

(iv) The final step:

A base to be used in this step may include hydrazide compound or its salt such as trimethylaminoacetohydrazide chloride, (1-pyridyl)acetohydrazide chloride and the like.

This step is usually carried out in a solvent which does not adversely influence the reaction such as tetrahydrofuran or the lower alkanol as aforementioned.

The reaction temperature is not critical but the reaction is usually carried out at ambient temperature.

The present invention may include within its scope, the cases that the protected amino group as a substituent of the acylamino group and/or the protected carboxy group are transformed into the corresponding free amino group and/or free carboxy group during the reaction or post-treatment in the processes as explained above.

The object compounds (I) obtained according to the Processes 1 to 11 as explained above can be used without any isolation in the subsequent processes.

Preparations A to C for the starting compound (II) are explained in detail as follows.

(A) Preparation A:

① Preparation ①:

The object compound (II-1) can be prepared by reacting the compound (II-a) with a compound of the formula: $R^3$—CHO, wherein $R^3$ is as defined above in a conventional manner.

The reaction is preferably carried out under an anhydrous condition.

The reaction can also be carried out in the presence of a base such as trialkylamine as aforementioned or an acid such as Lewis acid as aforementioned.

The reaction is usually carried out in a conventional solvent which does not adversely influence the reaction such as benzene, xylene, N,N-dimethylformamide, and the like, and the reaction temperature is not critical and the reaction is usually carried out at ambient temperature to under heating.

② Preparation ②:

The object compound (II-2) can be prepared by halogenating the compound (II-1) in a conventional manner.

A halogenating agent to be used in this reaction may be one which can halogenate a hydroxy group such as phosphorus halide (e.g. phosphorus trichloride, phosphorus tribromide, phosphorus pentachloride, phosphorus oxychloride, etc.), thionyl chloride, phosgene, and the like.

The reaction is usually carried out in the presence of a base as aforementioned in Process 3 in a conventional solvent which does not adversely influence the reaction such as methylene chloride, chloroform, and the like, and the reaction temperature is not critical and the reaction is usually carried out under cooling to at ambient temperature.

③ Preparation ③:

The object compound (II-3) can be prepared by azidating the compound (II-2) in a conventional manner.

An azidating agent to be used in this reaction may include hydrogen azide or a salt thereof (e.g. sodium azide, tetramethylguanidium azide, etc.), and the like.

The reaction is usually carried out in a conventional solvent which does not adversely influence the reaction such as methylene chloride, chloroform, N,N-dimethylformamide, and the like, and the reaction temperature is not critical and the reaction is usually carried out under cooling to at ambient temperature.

④ Preparation ④:

The object compound (II-4) can be prepared by reacting the compound (II-3) with a silver salt of an acid in a conventional manner.

The silver salt of an acid to be used in this reaction may include silver fluoroborate, silver perchlorate, and the like.

The reaction is preferably carried out in the presence of an acid as aforementioned in Process 1.

The reaction is usually carried out in a conventional solvent which does not adversely influence the reaction such as water, tetrahydrofuran and the like, and the reaction temperature is not critical and the reaction is usually carried out under cooling to at ambient temperature.

⑤ Preparation ⑤:

The object compound (II-5) can be prepared by introducing a mercapto-protective group into the compound (II-4) in a conventional manner.

This reaction can also be carried out by transforming the compound (II-4) to a compound having a free mercapto group with hydrogen sulfide and then introducing the mercapto-protective group, and this reaction is included within this process.

This reaction is substantially the same as those illustrated for the acylation reaction of the compound (I-3) in Process 3, and therefore is to be referred to said explanation.

(B) Preparation B:

① Preparation ①:

The object compound (II-6) can be prepared by introducing a mercapto-protective group into the compound (II-b) in a conventional manner.

This reaction is substantially the same as those illustrated for the acylation reaction of the compound (I-3) in Process 3, and therefore is to be referred to said explanation.

② Preparation ②:

The object compound (II-7) can be prepared by reacting the compound (II-6) with a base in a conventional manner.

A base to be used in this reaction may include one as aforementioned in Process 3.

The reaction is usually carried out in a conventional solvent which does not adversely influence the reaction such as benzene, toluene, and the like, and the reaction temperature is not critical and the reaction is usually carried out at ambient temperature.

③ Preparation ③:

The object compound (II-8) can be prepared by reacting the compound (II-7) with ozone and then degrading the resultant ozonide in a conventional manner.

The ozonide produced by the compound (II-7) and ozone is usually reduced by dimethyl sulfide, trimethylphosphite, sodium bisulfite, sodium sulfite and the like.

This reaction is usually carried out in a conventional solvent which does not adversely influence the reaction such as ethyl acetate and the like, and the reaction temperature is not critical and the reaction is usually carried out under cooling.

④ Preparation ④:

The object compound (II-9) can be prepared by reducing the compound (II-8) in a conventional manner.

A reducing agent to be used in this reaction may include conventional reducing agent which can reduce an oxo group to a hydroxy group such as alkali metal borohydride (e.g. sodium borohydride, sodium cyanoborohydride, etc.), borane complex as aforementioned in Process 2, diborane, alminum-amalgam and the like.

This reaction is usually carried out in a conventional solvent which does not adversely influence the reaction such as tetrahydrofuran and the like, and the reaction temperature is not critical and the reaction is usually carried out under cooling.

⑤ Preparation ⑤:

The object compound (II-10) can be prepared by halogenating the compound (II-9) in a conventional manner.

This reaction is substantially the same as that of Preparation A-②, and therefore the halogenating agent and the reaction conditions (e.g. solvent, reaction temperature, etc.) are to be referred to said explanation.

⑥ Preparation ⑥:

The object compound (II-5) can be prepared by azidating the compound (II-10) in a conventional manner.

This reaction is conventional and substantially the same as that of Preparation A-③, and therefore the azidating agent and the reaction condition (e.g. solvent, reaction temperature, etc.) are to be referred to said explanation.

(C) Preparation C:

① Preparation ①:

The object compound (II-11) can be prepared by reducing the compound (II-5) in a conventional manner.

The reduction method of this reaction is substantially the same as that of the reduction in Process 1, and therefore the reducing agent and the reaction conditions (e.g. solvent, reaction temperature, etc.) are to be referred to said explanation, and further reducing agent to be used in the reaction may include hydrogen sulfide in the presence of a base as aforementioned in Process 3.

② Preparation ②:

The object compound (II-12) can be prepared by formylating the compound (II-11) in a conventional manner.

This reaction is substantially the same as those in Process 3, and therefore the reaction conditions (e.g. solvent, reaction temperature, etc.) are to be referred to said explanation.

③ Preparation ③:

The object compound (II) can be prepared by reacting the compound (II-12) with a dehydrating agent in a conventional manner.

A dehydrating agent to be used in this reaction may include conventional one such as phosphorus halocompound (e.g. phosphorus trichloride, phosphorus tribromide, phosphorus oxychloride, phosphorus pentachloride, etc.), triphenylphosphine dibromide, phosphorus pentoxide, phosgene, thionyl chloride, trichloromethyl chloroformate, isocyanuric chloride, sulfonyl halide (e.g. benzenesulfonyl chloride, toluenesulfonyl chloride etc.) and the like.

This reaction is preferably carried out in the presence of a base as aforementioned in Process 3.

Further this reaction is usually carried out in a conventional solvent which does not adversely influence the reaction such as methylene chloride, chloroform, and the like, and the reaction temperature is not critical and the reaction is usually carried out under cooling to at ambient temperature.

It is to be noted that, in the aforementioned reactions including the Processes 1 to 11 and Preparations A to C and/or the post-treatment of the reaction mixture, in case that the compound possesses optical and/or geometrical isomer, it may occasionally be transformed into the other optical and/or geometrical isomer and such case is also included within the scope of the present invention.

In case that the object compounds (I) have a free carboxy group at the 2nd position thereof and/or a free amino group at the 7th position thereof, it may be transformed into its pharmaceutically acceptable salts by a conventional method.

The object compounds (I) and pharmaceutically acceptable salts thereof of the present invention are novel and exhibit high antimicrobial activity, inhibiting the growth of a wide variety of pathogenic microorganisms, especially fungus.

For example, sodium 7-phenoxyacetamido-8-oxo-5-thia-1,3-diazabicyclo[4,2,0]oct-3-ene-2-carboxylate exhibits antimicrobial activities against *Candida albicans* Yu-1200 and *Trichophyton asteroides*, and 7-phenoxyacetamido-8-oxo-3-hydroxy-5-thia-1,3-diazabicyclo[4,2,0]octane-2-carboxylic acid exhibits those against *Staphylococcus aureus* 209P JC-1 in addition to the above fungi.

Further, the object compounds (I) are also useful intermediates for preparing antimicrobial agents such as the above compounds.

For therapeutic administration, the object compounds (I) and pharmaceutically acceptable salts thereof of the present invention are used in the form of conventional pharmaceutical preparation which contains said compound, as active ingredients, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compounds (I) to be applied, etc. In general, amounts between 1 mg. and about 4000 mg. or even more per day may be administered to a patient. An average single dose of about 50 mg., 100 mg., 250 mg., 500 mg., 1000 mg., 2000 mg. of the object compounds (I) of the present invention may be used in treating diseases infected by pathogenic microorganisms.

The following examples are given for the purpose of illustrating the present invention:

PREPARATION OF THE OBJECT COMPOUNDS

Example 1

To a solution of benzyl 2-[3-phenoxyacetamido-4-(2,2,2-trichloroethoxycarbonylthio)-2-oxo-1-azetidinyl]-2-isocyanoacetate (2.20 g.) in N,N-dimethylformamide (15 ml.) was added zinc powder (3.30 mg.) at 0° C., and the mixture was stirred at the same temperature for 10 minutes. Thereto was added dropwise acetic acid (2.0 ml.) over a period of 3 minutes and the mixture was stirred at 0° C. for 25 minutes. The reaction mixture was diluted with ethyl acetate (50 ml.) and filtered through a pad of Celite. To the filtrate was added ethyl acetate (50 ml.) and washed with a mixture of 5 to 6% aqueous solution of sodium bicarbonate (60 ml.) and a saturated aqueous solution of sodium chloride (30 ml.), a dilute aqueous solution of sodium chloride (30 ml.×2), a saturated aqueous solution of sodium chloride (30 ml.), water (50 ml.) and a saturated aqueous solution of sodium chloride successively. Drying and removal of the solvent left an amorphous solid (1.51 g.). Chromatography on silica gel (15 g.) with a mixed solvent of methylene chloride and ethyl acetate (5:1 by volume) as an eluent and crystallization from diethyl ether gave benzyl 7-phenoxyacetamido-8-oxo-5-thia-1,3-diazabicyclo[4,2,0]oct-3-ene-2-carboxylate (750 mg.), mp 141.5°–143.0° C.

I.R. ($CH_2Cl_2$): 3390, 1785, 1745, 1690, 1600 cm$^{-1}$

N.M.R. δppm ($CDCl_3$): 4.56 (2H, s), 5.25 (2H, s), 5.32 (1H, d, J=4 Hz), 5.73 (1H, dd, J=4, 9 Hz), 6.00 (1H, d, J=2 Hz), 6.8–7.6 (10H, m), 8.28 (1H, d, J=2 Hz)

Example 2

(1) To a solution of benzyl 7-phenoxyacetamido-8-oxo-5-thia-1,3-diazabicyclo[4,2,0]oct-3-ene-2-carboxylate (3.0 g.) in tetrahydrofuran (22 ml.) was added alminum amalgam at 4° C., which was prepared by alminium power (1.8 g.) and 0.5% mercuric chloride (4 ml.), and water (0.75 ml.) was added dropwise thereto. After the mixture was stirred at 10° C. for 75 minutes under nitrogen atmosphere, the reaction mixture was diluted with ethyl acetate (50 ml.) and filtered through a pad of Celite. The filter cake was washed with ethyl acetate, and the filtrate and washings were combined, washed twice with an aqueous solution of sodium chloride, dried over magnesium sulfate and evaporated to leave an oil (2.7 g.). Chromatography on silica gel (15 g.) with a mixed solvent of methylene chloride and ethyl acetate (5:1 by volume) as an eluent gave an amorphous solid (2.64 g.) of benzyl 7-phenoxyacetamido-8-oxo-5-thia-1,3-diazabicyclo[4,2,0]octane-2-carboxylate.

I.R. ($CH_2Cl_2$): 3390, 3325, 1775, 1745, 1690 cm$^{-1}$

N.M.R. δppm ($CDCl_3$): 2.10 (1H, broad s), 4.27 (2H, AB$_q$, J=14 Hz), 4.50 (2H, s), 5.20 (2H, s), 5.38 (1H, s), 5.42 (1H, d, J=5 Hz), 5.75 (1H, dd, J=9.5, 5 Hz), 6.8–7.7 (10H, m)

(2) The same object product (30 mg.) as that of Example 2-(1) was obtained by reducing the same starting compound (85 mg.) as that of Example 2-(1) with sodium borohydride (24 mg.) in acetic acid (72 μl), methylene chloride (2 ml.) and tetrahydrofuran (1 ml.) in substantially the same manner as that of Example 2-(1).

Example 3

(1) A solution of benzyl 7-phenoxyacetamido-8-oxo-5-thia-1,3-diazabicyclo[4,2,0]octane-2-carboxylate (5.86 g.) and 2,6-lutidine (3.20 ml.) in methylene chloride (29 ml.) was cooled to −78° C. and trifluoromethanesulfonic anhydride (2.44 ml.) was added thereto over a period of 3 minutes. The resultant solution was allowed to warm to 0° C. over a period of 75 minutes and kept at 0° C. for additional 10 minutes. The reaction mixture was poured into chilled dilute phosphoric acid and extracted with ethyl acetate (150 ml.). The extract was washed with dilute phosphoric acid, a dilute aqueous solution of sodium chloride, a saturated aqueous solution of sodium bicarbonate, a dilute aqueous solution of sodium chloride and a saturated aqueous solution of sodium chloride, successively. Drying and removal of the solvent left an amorphous solid (7.2 g.), which was chromatographed on silica gel (14 g.) with a mixed solvent of ethyl acetate and methylene chloride (2 to 25% by volume) as an eluent to give benzyl 7-phenoxyacetamido-8-oxo-3-trifluoromethanesulfonyl-5-thia-1,3-diazabicyclo[4,2,0]octane-2-carboxylate (4.49 g.).

I.R. ($CH_2Cl_2$): 3390, 1795, 1750, 1695 cm$^{-1}$

N.M.R. δppm ($CDCl_3$): 4.48 (2H, s), 4.82 (2H, s), 5.23 (2H, s), 5.32 (1H, d, J=5 Hz), 5.84 (1H, dd, J=9, 5 Hz), 6.18 (1H, s), 6.8–7.5 (10H, m)

(2) Benzyl 7-phenoxyacetamido-8-oxo-3-acetyl-5-thia-1,3-diazabicyclo[4,2,0]octane-2-carboxylate (580 mg.) was obtained by reacting benzyl 7-phenoxyacetamido-8-oxo-5-thia-1,3-diazabicyclo[4,2,0]octane-2-carboxylate (670 mg.) with acetyl chloride (0.16 ml.) in substantially the same manner as that of Example 3-(1).

I.R. ($CH_2Cl_2$): 3390, 1785, 1745, 1690 cm$^{-1}$

N.M.R. δppm (DMSO-d$_6$): 2.16 (3H, s), 4.57 (2H, s), 4.96 (2H, AB$_q$, J=15 Hz), 5.22 (3H, s), 5.42 (1H, d, J=4 Hz), 5.56 (1H, dd, J=8, 4 Hz), 6.5–7.6 (10H, m), 9.16 (1H, d, J=8 Hz)

Example 4

To a solution of benzyl 7-phenoxyacetamido-8-oxo-3-trifluoromethanesulfonyl-5-thia-1,3-diazabicyclo[4,2,0]octane-2-carboxylate (1.50 g.) and N,N-dimethylaniline (0.41 ml.) in methylene chloride (30 ml.) was added phosphorus pentachloride (1.115 g.) at −35° C. under nitrogen atmosphere, and the mixture was stirred at −30° to −25° C. for 2.3 hours. The reaction mixture was cooled to −55° C., and thereto was added methanol (2.4 ml.). This mixture was allowed to warm to 0° C. over a period of 2 hours. Thereto was added water (2.4 ml.), and after stirring at 0° C. for an hour, the reaction mixture was poured into ice-water and extracted twice with ethyl acetate (120 ml. and 50 ml.). The combined extracts were washed with a small amount of water, a dilute aqueous solution of potassium dihydrogenphosphate, a phosphate buffer solution (pH 7, ×2) and an aqueous solution of sodium chloride, successively. After drying over magnesium sulfate and filtration, to the filtrate was added p-toluenesulfonic acid monohydrate (509 mg.) and concentrated to give a crystalline residue, to which diethyl ether was added. The crystals were collected by filtration and washed with diethyl ether to afford p-toluenesulfonic acid salt of benzyl 7-amino-8-oxo-3-trifluoromethanesulfonyl-5-thia-1,3-diazabicyclo[4,2,0]octane-2-carboxylate (1.365 g.), mp 155°-158° C. (dec.).

I.R. (Nujol): 1795, 1770 cm$^{-1}$

N.M.R. δppm (DMSO-d$_6$): 2.34 (1H, s), 5.03 (1H, d, J=15.5 Hz), 5.32 (2H, s), 5.32 (1H, d, J=5 Hz), 5.36 (1H, d, J=15.5 Hz), 5.60 (1H, d, J=5 Hz), 6.60 (1H, s), 7.17 (2H, d, J=8 Hz), 7.46 (5H, s), 7.56 (2H, d, J=8 Hz)

Example 5

(1) To a suspension of p-toluenesulfonic acid salt of benzyl 7-amino-8-oxo-3-trifluoromethanesulfonyl-5-thia-1,3-diazabicyclo[4,2,0]octane-2-carboxylate (800 mg.) in methylene chloride (8 ml.) was added pyridine (146 μl). After stirring at −55° C. for 5 minutes, 2-(2-thienyl)acetyl chloride (290 mg.) was added thereto, and then the mixture was gradually allowed to warm to 0° C. over a period of 1.5 hours. The mixture was poured into chilled dilute hydrochloric acid and extracted with ethyl acetate (50 ml.). The extract was washed with water (×2), a dilute aqueous solution of sodium bicarbonate, water and an aqueous solution of sodium chloride, successively. Drying over magnesium sulfate and removal of the solvent left an amorphous solid (800 mg.), which was chromatographed on silica gel (10 g.) with a mixed solvent of methylene chloride and ethyl acetate (95:5 to 90:10 by volume) to give benzyl 7-[2-(2-thienyl)acetamido]-8-oxo-3-trifluoromethanesulfonyl-5-thia-1,3-diazabicyclo[4,2,0]octane-2-carboxylate (667 mg.).

I.R. (CH$_2$Cl$_2$): 3400, 1800, 1750, 1690 cm$^{-1}$

N.M.R. δppm (CDCl$_3$): 3.80 (2H, s), 4.80 (2H, s), 5.22 (2H, s), 5.25 (1H, d, J=4.5 Hz), 5.72 (1H, d d, J=9, 4.5 Hz), 6.11 (1H, s), 6.44 (1H, d, J=9 Hz), 6.9-7.7 (8H, m)

(2) Benzyl 7-[2-(2-thienyl)acetamido]-7-methoxy-8-oxo-3-trifluoromethanesulfonyl-5-thia-1,3-diazabicyclo[4,2,0]octane-2-carboxylate (317 mg.) was obtained by reacting benzyl 7-amino-7-methoxy-8-oxo-3-trifluoromethanesulfonyl-5-thia-1,3-diazabicyclo[4,2,0]octane-2-carboxylate (308 mg.) with 2-(2-thienyl)acetyl chloride (200 mg.) in substantially the same manner as that of Example 5-(1).

I.R. (CH$_2$Cl$_2$): 3390, 1790, 1755, 1695 cm$^{-1}$

N.M.R. δppm (CDCl$_3$): 3.38 (3H, s), 3.85 (2H, s), 4.72 (2H, s), 5.28 (2H, s), 5.47 (1H, s), 6.17 (1H, s), 6.75-7.5 (4H, m), 7.35 (5H, s)

(3) Benzyl 7-phenoxyacetamido-7-methoxy-8-oxo-3-trifluoromethanesulfonyl-5-thia-1,3-diazabicyclo[4,2,0]octane-2-carboxylate (394 mg.) was obtained by reacting benzyl 7-amino-7-methoxy-8-oxo-3-trifluoromethanesulfonyl-5-thia-1,3-diazabicyclo[4,2,0]octane-2-carboxylate (377 mg.) with phenoxyacetyl chloride (166 μl) in substantially the same manner as that of Example 5-(1).

I.R. (CH$_2$Cl$_2$): 3380, 1790, 1755, 1700 cm$^{-1}$

N.M.R. δppm (CDCl$_3$): 3.45 (3H, s), 4.58 (2H, s), 4.76 (2H, s), 5.32 (2H, s), 5.50 (1H s), 6.23 (1H, s), 5.8-7.8 (11H, m)

Example 6

(1) To a solution of benzyl 7-phenoxyacetamido-8-oxo-3-trifluoromethanesulfonyl-5-thia-1,3-diazabicyclo[4,2,0]octane-2-carboxylate (88 mg.) in methylene chloride (2 ml.) was added a solution of 1,5-diazabicyclo[5,4,0]undec-5-ene (24 mg.) in methylene chloride (0.5 ml.) at −20° C. After stirring at the same temperature for 45 minutes, the reaction mixture was poured into a chilled phosphate buffer solution (pH 7) and then extracted with ethyl acetate. The extract was washed with water and an aqueous solution of sodium chloride. Drying over magnesium sulfate and removal of the solvent left an oil (69 mg.), which was chromatographed on silica gel (2 g.) with a mixed solvent of benzene and ethyl acetate (5:1 by volume) to give an oil (33 mg.) of benzyl 7-phenoxyacetamido-8-oxo-5-thia-1,3-diazabicyclo[4,2,0]oct-2-ene-2-carboxylate.

N.M.R. δppm (CDCl$_3$): 4.57 (2H, s), 4.88 (2H, AB$_q$, J=9 Hz), 5.10 (1H, d, J=6 Hz), 5.38 (2H, s), 6.05 (1H, d d, J=10, 6 Hz) 6.8–7.7 (10H, m)

(2) 4-Nitrobenzyl 7-phenoxyacetamido-8-oxo-5-thia-1,3-diazabicyclo[4,2,0]-oct-2-ene-2-carboxylate (70 mg.) was obtained by reacting 4-nitrobenzyl 7-phenoxyacetamido-8-oxo-3-trifluoromethanesulfonyl-5-thia-1,3-diazabicyclo[4,2,0]octane-2-carboxylate (120 mg.) with 1,5-diazabicyclo[5,4,0]undec-5-ene (30 mg.) as a base in substantially the same manner as that of Example 6-(1).

I.R. (CH$_2$Cl$_2$): 3390, 1810, 1750, 1695, 1640 cm$^{-1}$

N.M.R. δppm (CDCl$_3$): 4.57 (2H, s), 4.90 (2H, d, J=4 Hz), 5.40 (1H, d, J=5.5 Hz), 5.44 (2H, s), 6.07 (1H, d d., J=9 and 5.5 Hz), 6.8–7.8 (6H, m), 7.59 (2H, d, J=8 Hz), 8.22 (2H, d, J=8 Hz)

(3) Pivaloyloxymethyl 7-phenoxyacetamido-8-oxo-5-thia-1,3-diazabicyclo[4,2,0]oct-2-ene-2-carboxylate (252 mg.) was obtained by reacting pivaloyloxymethyl 7-phenoxyacetamido-8-oxo-3-trifluoromethanesulfonyl-5-thia-1,3-diazabicyclo[4,2,0]octane-2-carboxylate (337 mg.) with 1,5-diazabicyclo[5,4,0]undec-5-ene (83 μl) as a base in substantially the same manner as that of Example 6-(1).

I.R. (CH$_2$Cl$_2$): 3400, 1810, 1755, 1695, 1640 cm$^{-1}$

N.M.R. δppm (CDCl$_3$): 1.20 (9H, s), 4.58 (2H, s), 4.93 (2H, AB$_q$), 5.17 (1H, d, J=5.5 Hz), 5.99 (2H, s), 6.12 (1H, d d, J=9, 5.5 Hz), 6.8–7.6 (6H, m)

(4) Methoxymethyl 7-phenoxyacetamido-8-oxo-5-thia-1,3-diazabicyclo[4,2,0]oct-2-ene-2-carboxylate (282 mg.) was obtained by reacting methoxymethyl 7-phenoxyacetamido-8-oxo-3-trifluoromethanesulfonyl-5-thia-1,3-diazabicyclo[4,2,0]octane-2-carboxylate (386.0 mg.) with 1,5-diazabicyclo[5,4,0]undec-5-ene (110 mg.) as a base in substantially the same manner as that of Example 6-(1).

I.R. (CH$_2$Cl$_2$): 3390, 1809, 1745, 1695, 1640, 1600 cm$^{-1}$

N.M.R. δppm (CDCl$_3$): 3.57 (3H, s), 4.61 (2H, s), 4.95 (2H, AB$_q$), 5.18 (1H, d, J=6 Hz), 5.52 (2H, s), 6.14 (1H, d d, J=9.5, 6 Hz), 6.8–7.6 (5H, m)

(5) Benzyl 7-[2-(2-thienyl)acetamido]-8-oxo-5-thia-1,3-diazabicyclo[4,2,0]oct-2-ene-2-carboxylate (190 mg.) was obtained by reacting benzyl 7-[2-(2-thienyl)acetamido]-8-oxo-3-trifluoromethanesulfonyl-5-thia-1,3-diazabicyclo[4,2,0]octane-2-carboxylate (630 mg.) with 1,5-diazabicyclo[5,4,0]undec-5-ene (173 mg.) as a base in substantially the same manner as that of Example 6-(1), mp 97° C. (dec.).

I.R. (KBr): 3280, 1795, 1740, 1655, 1625 cm$^{-1}$

N.M.R. δppm (CDCl$_3$): 3.88 (2H, s), 4.87 (2H, AB$_q$, J=17 Hz), 5.06 (1H, d, J=5 Hz), 5.37 (2H, s), 6.00 (1H, d d, J=9, 5 Hz), 6.48 (1H, d, J=9 Hz), 7.0–7.6 (8H, m)

(6) Benzyl 7-phenoxyacetamido-8-oxo-5-thia-1,3-diazabicyclo[4,2,0]oct-2-ene-2-carboxylate-5-oxide (6 mg.) was obtained by reacting benzyl 7-phenoxyacetamido-8-oxo-3-trifluoromethanesulfonyl-5-thia-1,3-diazabicyclo[4,2,0]octane-2-carboxylate-5-oxide (34 mg.) with 1,5-diazabicyclo[5,4,0]undec-5-ene (9 mg.) as a base in substantially the same manner as that of Example 6-(1).

I.R. (CH$_2$Cl$_2$): 1820, 1740, 1700, 1640, 1600 cm$^{-1}$ (7) Pivaloyloxymethyl 7-phenoxyacetamido-8-oxo-5-thia-1,3-diazabicyclo[4,2,0]oct-2-ene-2-carboxylate-5-oxide (204 mg.) was obtained by reacting pivaloyloxymethyl 7-phenoxyacetamido-8-oxo-3-trifluoromethanesulfonyl-5-thia-1,3-diazabicyclo[4,2,0]octane-2-carboxylate-5-oxide (404 mg.) with 1,5-diazabicyclo[5,4,0]undec-5ene (98.5 μl) as a base in substantially the same manner as that of Example 6-(1).

I.R. (CHCl$_3$): 1820, 1750, 1690, 1635, 1595 cm$^{-1}$

N.M.R. δ ppm (CDCl$_3$): 1.25 (9H, s), 4.1–5.1 (2H, m), 4.60 (2H, s), 5.30 (1H, d, J=18 Hz), 6.00 (2H, s), 6.36 (1H, d d, J=10, 5 Hz), 6.8–7.6 (5H, m), 7.95 (1H, d, J=10 Hz)

Example 7

(1) To a solution of benzyl 7-phenoxyacetamido-8-oxo-3-trifluoromethanesulfonyl-5-thia-1,3-diazabicyclo[4,2,0]octane-2-carboxylate (2.19 g.) and anisole (6.3 ml.) in methylene chloride (20 ml.) was added a solution of aluminum trichloride (2.6 g.) in nitromethane (10 ml.) at 0° C. over a period of 5 minutes. The resultant deep red solution was stirred at 0° C. for 30 minutes. After the reaction mixture was poured into a mixture of ice and ethyl acetate (120 ml.), it was acidified to pH 1 with 3 N hydrochloric acid. The organic layer was separated, washed twice with an aqueous solution of sodium chloride and hydrochloric acid and then extracted with a chilled dilute aqueous solution of sodium bicarbonate (once with 50 ml. and twice with 30 ml.). These aqueous extracts were combined, acidified to pH 1 with 3 N hydrochloric acid, saturated with sodium chloride and then extracted three times with chloroform. Drying over magnesium sulfate and removal of the solvent afforded an amorphous solid (1.75 g.) of 7-phenoxyacetamido-8-oxo-3-trifluoromethanesulfonyl-5-thia-1,3-diazabicyclo[4,2,0]octane-2-carboxylic acid.

I.R. (CH$_2$Cl$_2$): 3390, 1800, 1770, 1750, 1730 cm$^{-1}$

N.M.R. δ ppm (CDCl$_3$): 4.60 (2H, s), 4.95 (2H, s), 5.46 (1H, d, J=5 Hz), 5.89 (1H, d d, J=10, 5 Hz), 6.24 (1H, s), 6.8–7.8 (6H, m)

(2) 7-Phenoxyacetamido-8-oxo-3-trifluoromethanesulfonyl-5-thia-1,3-diazabicyclo[4,2,0]octane-2-carboxylic acid-5-oxide (877 mg.) was obtained by reacting benzyl 7-phenoxyacetamido-8-oxo-3-trifluoromethanesulfonyl-5-thia-1,3-diazabicyclo[4,2,0]octane-2-carboxylate-5-oxide (1.08 g.) with aluminum trichloride (1.25 g.) and anisole (3.04 ml.) in substantially the same manner as that of Example 7-(1).

I.R. (CH$_2$Cl$_2$): 1805, 1750 (shoulder), 1730, 1695 cm$^{-1}$

N.M.R. δ ppm (DMSO-d$_6$): 4.63 (2H, s), 5.05 (2H, AB$_q$, J=20 Hz), 5.15 (1H, d, J=5 Hz), 5.92 (1H, d d, J=10.5, 5 Hz), 6.30 (1H, s), 6.7–7.5 (5H, m), 8.30 (1H, d, J=10.5 Hz)

(3) To a cooled solution of benzyl 7-phenoxyacetamido-8-oxo-3-acetyl-5-thia-1,3-diazabicyclo[4,2,0]octane-2-carboxylate (300 mg.) in tetrahydrofuran (9 ml.) was added an aqueous solution (8 ml.) of sodium carbonate (107 mg.). The mixture was stirred at 0° C. for 75 minutes and at room temperature for additional 30 minutes. After removal of the tetrahydrofuran, the remaining aqueous layer was washed with ethyl acetate, acidified to pH 2 with 1 N hydrochloric acid and extracted three times with methylene chloride. Drying over magnesium sulfate and removal of the solvent gave an amorphous solid (235 mg) of 7-phenoxyacetamido-8-oxo-3-acetyl-5-thia-1,3-diazabicyclo[4,2,0]octane-2-carboxylic acid.

I.R. (CH$_2$Cl$_2$): 1785, 1760 (shoulder), 1740 (shoulder), 1690 cm$^{-1}$

| N.M.R. δ ppm (CD$_3$OD) | 2.20 (s) ⎫ (3H), 2.40 (s) ⎭ 4.1–5.2 (4H, m), 5.3–5.8 (3H, m), 6.7–7.4 (5H, m) |
|---|---|

(4) 7-Phenoxyacetamido-8-oxo-3-hydroxy-5-thia-1,3-diazabicyclo[4,2,0]octane-2-carboxylic acid (160 mg.) was obtained by hydrolyzing benzyl 7-phenoxyacetamido-8-oxo-3-hydroxy-5-thia-1,3-diazabicyclo[4,2,0]octane-2-carboxylate (288 mg.) with sodium carbonate (131 mg.) in substantially the same manner as that of Example 7-(3), mp 129°–135° C. (dec.).

I.R. (CHCl$_3$): 3390, 1780, 1740 (shoulder), 1695 cm$^{-1}$

N.M.R. δ ppm (acetone-d$_6$): 3.95 (1H, broad s), 4.62 (2H, AB$_q$, J=14 Hz), 4.67 (2H, s), 5.50 (1H, d, J=4 Hz), 5.68 (1H, s), 5.76 (1H, d d, J=9, 4 Hz), 6.9–7.6 (5H, m), 8.22 (1H, d, J=9 Hz)

(5) To a solution of benzyl 7-phenoxyacetamido-8-oxo-5-thia-1,3-diazabicyclo[4,2,0]oct-3-ene-2-carboxylate (400 mg.) in tetrahydrofuran (12 ml.) was added a solution of potassium carbonate (195 mg.) in water (12 ml.) at 0° C. After the mixture was stirred at the same temperature for an hour and at room temperature for 1.8 hours, the reaction mixture was neutralized to pH 7 with cation-exchange resin Amberlite IRC-50 (TM; manufactured by Rohm & Haas Co., Ltd.) and then filtered. The filtrate was concentrated and lyophilized to give a powder (388 mg.) of potassium 7-phenoxyacetamido-8-oxo-5-thia-1,3-diazabicyclo[4,2,0]oct-3-ene-2-carboxylate.

I.R. (KBr): 1765, 1675, 1632, 1550 cm$^{-1}$

N.M.R. (DMSO-d$_6$+CD$_3$OD): 4.64 (2H, s), 5.34 (1H, d, J=5 Hz), 5.47 (1H, d, J=5 Hz), 5.58 (1H, d, J=2.5 Hz), 6.7–7.5 (5H, m), 8.22 (1H, d, J=2.5 Hz)

(6) Sodium 7-phenoxyacetamido-8-oxo-5-thia-1,3-diazabicyclo[4,2,0]oct-3-ene-2-carboxylate was obtained by hydrolyzing benzyl 7-phenoxyacetamido-8-oxo-5-thia-1,3-diazabicyclo[4,2,0]oct-3-ene-2-carboxylate with sodium carbonate in substantially the same manner as that of Example 7-(5).

I.R. (Nujol): 1760, 1640 (broad) cm$^{-1}$

N.M.R. δ ppm (DMSO-d$_6$): 4.60 (2H, s), 5.25–5.5 (3H, m), 6.7–7.6 (5H, m), 8.22 (1H, d, J=2 Hz)

Example 8

(1) To a solution of 7-phenoxyacetamido-8-oxo-3-trifluoromethanesulfonyl-5-thia-1,3-diazabicyclo[4,2,0]octane-2-carboxylic acid (547 mg.) in N,N-dimethylformamide (4 ml.) were added triethylamine (160 μl) and 4-nitrobenzyl bromide (276 mg.) at 0° C., and the mixture was stirred at room temperature for 18.5 hours. The reaction mixture was poured into a chilled dilute hydrochloric acid and then extracted with ethyl acetate (50 ml.). The extract was washed with water (×3), a dilute aqueous solution of sodium bicarbonate (×2), water and an aqueous solution of sodium chloride, successively. Drying over magnesium sulfate and removal of the solvent gave a residue (610 mg.), which was chromatographed on silica gel (9.5 g.) with a mixed solvent of benzene and ethyl acetate (10:1 to 5:1 by volume) to give an amorphous solid (328 mg.) of 4-nitrobenzyl 7-phenoxyacetamido-8-oxo-3-trifluoromethanesulfonyl-5-thia-1,3-diazabicyclo[4,2,0]octane-2-carboxylate.

I.R. (CH$_2$Cl$_2$): 3390, 1800, 1755, 1695 cm$^{-1}$

N.M.R. δ ppm (CDCl$_3$): 4.58 (2H, s), 4.95 (2H, s), 5.40 (2H, s), 5.43 (1H, d, J=4 Hz), 5.93 (1H, d.d, J=9, 4 Hz), 6.29 (1H, s), 6.8–7.7 (6H, m), 7.54 (2H, d, J=9 Hz), 8.28 (2H, d, J=9 Hz)

(2) Pivaloyloxymethyl 7-phenoxyacetamido-8-oxo-3-trifluoromethanesulfonyl-5-thia-1,3-diazabicyclo[4,2,-0]octane-2-carboxylate (375 mg.) was obtained by reacting 7-phenoxyacetamido-8-oxo-3-trifluoromethanesulfonyl-5-thia-1,3-diazabicyclo[4,2,0]octane-2-carboxylic acid (550 mg.) with iodomethyl pivalate (312 mg.) in substantially the same manner as that of Example 8-(1).

I.R. (CH$_2$Cl$_2$): 3390, 1800, 1760 (shoulder), 1700 cm$^{-1}$

N.M.R. δ ppm (CDCl$_3$): 1.20 (9H, s), 4.55 (2H, s), 4.92 (2H, s), 5.42 (1H, d, J=5 Hz), 5.87 (2H, AB quartet), 5.90 (1H, d.d, J=9, 5 Hz), 6.23 (1H, s), 6.8–7.6 (6H, m)

(3) Methoxymethyl 7-phenoxyacetamido-8-oxo-3-trifluoromethanesulfonyl-5-thia-1,3-diazabicyclo[4,2,0]octane-2-carboxylate (333 mg.) was obtained by reacting 7-phenoxyacetamido-8-oxo-3-trifluoromethanesulfonyl-5-thia-1,3-diazabicyclo[4,2,0]-octane-2-carboxylic acid (672 mg.) with methoxymethyl chloride (110 μl) in substantially the same manner as that of Example 8-(1).

I.R. (CH$_2$Cl$_2$): 3400, 1800, 1760, 1700 cm$^{-1}$

N.M.R. δ ppm (CDCl$_3$): 3.53 (3H, s), 4.59 (2H, s), 4.98 (2H, s), 5.41 (2H, s), 5.47 (1H, d, J=4.5 Hz), 5.95 (1H, d.d, J=9, 4.5 Hz), 6.25 (1H, s), 6.8–7.7 (6H, m)

(4) Pivaloyloxymethyl 7-phenoxyacetamido-8-oxo-3-trifluoromethanesulfonyl-5-thia-1,3-diazabicyclo[4,2,-0]octane-2-carboxylate-5-oxide (467 mg.) was obtained by reacting 7-phenoxyacetamido-8-oxo-3-trifluoromethanesulfonyl-5-thia-1,3-diazabicyclo[4,2,0]octane-2-carboxylic acid-5-oxide (748 mg.) with iodomethyl pivalate (710 mg.) in substantially the same manner as that of Example 8-(1).

I.R. (CH$_2$Cl$_2$): 3370, 1810, 1765, 1700 cm$^{-1}$

N.M.R. δ ppm (CDCl$_3$): 1.23 (9H, s), 4.55 (2H, s), 4.83 (1H, d, J=4 Hz), 4.88 (2H, AB$_q$, J=12 Hz), 5.87 (2H, s), 6.10 (1H, d.d, J=10, 4 Hz), 6.32 (1H, s), 6.8–7.5 (5H, m), 8.06 (1H, d, J=10 Hz)

Example 9

(1) A mixture of benzyl 7-phenoxyacetamido-8-oxo-5-thia-1,3-diazabicyclo[4,2,0]octane-2-carboxylate (635 mg.) and cupric sulfate pentahydrate (75 mg.) in a mixed solution of acetic acid (4 ml.) and water (0.4 ml.) was stirred at room temperature. After stirring for 10 minutes, an additional cupric sulfate pentahydrate (300 mg.) was added thereto and the mixture was stirred for additional 1.5 hours. The reaction mixture was cooled to 10° C. and sodium bisulfide (86 mg.) was added thereto. The resultant mixture was filtered through a pad of Celite and the filtrate was concentrated. The residue was taken up into ethyl acetate, washed with a dilute aqueous solution of sodium bicarbonate and an aqueous solution of sodium chloride. Drying over magnesium sulfate and removal of the solvent gave a residue (648 mg.), which was chromatographed on silica gel (20 g.) with a mixed solvent of benzene and ethyl acetate (5:1 to 2:1 by volume) to give an oil (307 mg.), which was crystallized from diethyl ether to afford benzyl 7-phenoxyacetamido-8-oxo-3-hydroxy-5-thia-1,3-diazabicyclo[4,2,0]octane-2-carboxylate (300 mg.), mp 184°–186° C.

I.R. (CH$_2$Cl$_2$): 3390, 1775, 1740, 1690 cm$^{-1}$

N.M.R. (CDCl$_3$): 3.73 (1H, broad s), 4.03 (1H, d, J=14 Hz), 4.56 (2H, s), 4.82 (1H, d, J=14 Hz), 5.04 (2H, s), 5.41 (1H, d, J=5 Hz), 5.64 (1H, s), 5.80 (1H, d.d, J=10, 5 Hz), 6.8–7.7 (11H, m)

(2) The same object product (15 mg.) as that of the Example 9-(1) was obtained by reacting the same starting compound (70 mg.) as that of Example 9-(1) with ferric chloride hexahydrate (46 mg.) in a mixture of acetic acid (0.5 ml.) and water (0.03 ml.) in substantially the same manner as that of Example 9-(1).

(3) The same object product (174 mg.) as that of Example 9-(1) was obtained by reacting the same starting compound (500 mg.) as that of Example 9-(1) with 2,3-dichloro-5,6-dicyano-1,4-benzoquinone (318 mg.) in benzene (10 ml.) in substantially the same manner as that of Example 9-(1).

Example 10

To a solution of benzyl 7-phenoxyacetamido-8-oxo-3-trifluoromethanesulfonyl-5-thia-1,3-diazabicyclo[4,2,-0]octane-2-carboxylate (1.172 g.) in methylene chloride (10 ml.) was added dropwise a solution of m-chloroperbenzoic acid (430 mg.) in methylene chloride (6 ml.) at 0° C. with stirring over a period of 20 minutes, and the mixture was stirred for an additional 15 minutes. The mixture was diluted with methylene chloride and washed with a chilled dilute aqueous solution of sodium bicarbonate and a mixture of a dilute aqueous solution of sodium chloride and an aqueous solution of sodium bicarbonate. Drying over magnesium sulfate and removal of the solvent left an amorphous solid (1.2 g.), which was chromatographed on silica gel (17 g.) with methylene chloride and then a mixed solvent of methylene chloride and ethyl acetate as an eluent to give an amorphous solid (1.10 g.) of benzyl 7-phenoxyacetamido-8-oxo-3-trifluoromethanesulfonyl-5-thia-1,3-diazabicyclo[4,2,0]octane-2-carboxylate-5-oxide.

I.R. (CH$_2$Cl$_2$): 3360, 1810, 1750, 1695 cm$^{-1}$

N.M.R. δ ppm (CDCl$_3$): 4.49 (2H, s), 4.60 (1H, d, J=14 Hz), 4.75 (1H, d, J=5 Hz), 5.05 (1H, broad d, J=14 Hz), 5.25 (2H, s), 6.03 (1H, d.d, J=10, 5 Hz), 6.28 (1H, broad s), 6.8–7.5 (10H, m), 8.03 (1H, broad d, J=10 Hz)

Example 11

P-Toluenesulfonic acid salt of benzyl 7-amino-8-oxo-3-trifluoromethanesulfonyl-5-thia-1,3-diazabicyclo[4,2,-0]octane-2-carboxylate (800 mg.) was partitioned between methylene chloride (50 ml.) and a chilled dilute aqueous solution of sodium bicarbonate. After said compound was completely dissolved in the methylene chloride layer, it was separated. The remaining aqueous solution was washed twice with methylene chloride (5 ml.), and the methylene chloride layer and washings were combined, dried over magnesium sulfate and evaporated to give a residue (550 mg.). This residue and 4-hydroxy-3,5-di-tertbutylbenzaldehyde (415 mg.) was dissolved in a mixture (30 ml.) of benzene and methylene chloride (3:1 by volume) and the solution was heated under reflux for 1.5 hours. After cooling to −15° C., magnesium sulfate (1.2 g.) was added thereto, followed by addition of nickel dioxide (780 mg.). The mixture was stirred at −10° C. for 30 minutes and at room temperature for additional 15 minutes. The reaction mixture was filtered through a pad of Celite and the filter cake was washed with methylene chloride. The filtrate and washings were combined and thereto was added methanol (10 ml.). The solution was allowed to stand at room temperature for 17.5 hours and evaporated to dryness. The resultant residue was dissolved in a mixture of methanol (15 ml.) and methylene chloride (5 ml.) and allowed to stand at room temperature for additional 8 hours. The reaction mixture was evaporated to dryness, and the residue was dissolved in a mixture of methanol (12 ml.) and tetrahydrofuran (6 ml.) and treated with Girard's Reagent T (370 mg.) at room temperature for 7 hours. The resultant mixture was concentrated and poured into a mixture of ethyl acetate (60 ml.) and water, and the separated organic layer was washed three times with water and once with an aqueous solution of sodium chloride. Drying over magnesium sulfate and removal of the solvent left an oil (0.7 g.), which was chromatographed on silica gel (8 g.) with a mixed solvent of benzene and ethyl acetate (10:1 by volume) as an eluent to give an oil (312 mg.) of benzyl 7-amino-7-methoxy-8-oxo-3-trifluoromethanesulfonyl-5-thia-1,3-diazabicyclo[4,2,0]octane-2-carboxylate.

I.R. ($CH_2Cl_2$): 1790, 1755 cm$^{-1}$

N.M.R. δ ppm ($CDCl_3$): 2.20 (2H, broad s), 3.43 (3H, s), 4.83 (2H, s), 5.11 (1H, s), 5.28 (2H, s), 6.20 (1H, s), 7.35 (5H, s)

PREPARATION OF THE STARTING COMPOUNDS

Preparation 1

Into a 500 ml. flask equipped with a Dean-Stark condenser filled with Molecular Sieves 3A (TM, manufactured by Nakarai Chemicals Ltd.) were charged with 3-phenoxymethyl-6-oxo-2-thia-4,7-diazabicyclo[3,2,0]hept-3-ene (995 mg.), benzyl glyoxylate (6.2 g.) and benzene (80 ml.). The mixture was heated under reflux for 3.5 hours. After benzene (40 ml.) was distilled off, the resultant solution was cooled to room temperature, and 25% aqueous solution of sodium bisulfite (150 ml.) was added thereto. The mixture was stirred for half an hour, and the precipitate was filtered off and washed with benzene. The organic layer was separated and washed twice with water (50 ml.) and twice with an aqueous solution of sodium chloride (150 ml.). Drying over magnesium sulfate and removal of the solvent gave an oil (8.7 g.) of 7-(1-benzyloxycarbonyl-1-hydroxymethyl)-3-phenoxymethyl-6-oxo-2-thia-4,7-diazabicyclo[3,2,0]hept-3-ene.

I.R. ($CH_2Cl_2$): 1780, 1645 cm$^{-1}$

Preparation 2

To a solution of 7-(1-benzyloxycarbonyl-1-hydroxymethyl)-3-phenoxymethyl-6-oxo-2-thia-4,7-diazabicyclo[3,2,0]hept-3ene (8.3 g.) and 2,6-lutidine (6.95 ml.) in methylene chloride (60 ml.) was added dropwise thionyl chloride (3.40 ml.) at −20° C. over a period of 5 minutes, and the reaction mixture was stirred at the same temperature for 20 minutes and then allowed to warm to room temperature. After stirring for 20 minutes, the mixture was poured into a chilled dilute hydrochloric acid and extracted with ethyl acetate (150 ml.). The extract was washed with diluted hydrochloric acid, water, a dilute aqueous solution of sodium chloride and a saturated aqueous solution of sodium chloride, successively. Drying over magnesium sulfate, filtration and removal of the solvent left a brown oil of 7-(1-benzyloxycarbonyl-1-chloromethyl)-3-phenoxymethyl-6-oxo-2-thia-4,7-diazabicyclo[3,2,0]hept-3-ene (8.8 g.).

The product was dissolved in anhydrous chloroform (50 ml.) and cooled to 0° C. To the solution was added tetramethylguanidium azide (7.6 g.) at a time, and stirred at room temperature for 30 minutes. The resultant solution was poured into a chilled dilute hydrochloric acid and extracted with ethyl acetate (300 ml.). The extract was washed with a dilute aqueous solution of sodium chloride (50 ml.×2), a saturated aqueous solution of sodium chloride, a dilute aqueous solution of sodium bicarbonate and a saturated aqueous solution of sodium chloride, successively. Drying over magnesium sulfate and removal of the solvent left a brown oil (8.0 g.), which was chromatographed on silica gel (250 g.) with a mixed solvent of benzene and acetone (95:5 by volume) as an eluent to give 7-(1-benzyloxycarbonyl-1-azidomethyl)-3-phenoxymethyl-6-oxo-2-thia-4,7-diazabicyclo[3,2,0]hept-3-ene (3.70 g.).

I.R. ($CH_2Cl_2$): 2130, 1785, 1755 cm$^{-1}$

N.MR. δ ppm ($CDCl_3$): 4.5–5.0 (2H, m), 5.16 (s), 5.43 (s), 5.20 (s), 5.52 (s) (2H), (1H), 5.68 (1H, m), 5.98 (1H, m), 6.7–7.5 (10H, m)

Preparation 3

To a cooled solution of 7-(1-benzyloxycarbonyl-1-azidomethyl)-3-phenoxymethyl-6-oxo-2-thia-4,7-diazabicyclo[3,2,0]hept-3-ene (3.0 g.) in tetrahydrofuran (48 ml.) was added silver tetrafluoroborate (2.05 g.), followed by a solution of p-toluenesulfonic acid (145.8 mg.) in water (8.1 ml.). After the resultant mixture was stirred at 0° C. for 9 hours, it was concentrated to a volume of 10 ml. To the concentrate was added a mixture of methanol (5 ml.) and water (10 ml.) and precipitates were triturated, filtered and washed with water (three times), a mixture of methanol (5 ml.) and water (10 ml.) (several times), methanol, diethyl ether and hexane, successively to give silver salt at the mercapto group of benzyl 2-azido-2-(3-phenoxyacetamido-4-mercapto-2-oxo-1-azetidinyl)acetate (3.75 g.).

I.R. (Nujol): 2120, 1780, 1750, 1660 (broad) cm$^{-1}$

Preparation 4

To a cooled solution of silver salt at the mercapto group of benzyl 2-azido-2-(3-phenoxyacetamido-4-mercapto-2-oxo-1-azetidinyl)acetate (3.08 g.) in hexamethylphosphoramide (12 ml.) was added 2,2,2-trichloroethyl chloroformate (1.15 ml.) over a period of 3 minutes, and the resultant mixture was stirred at room temperature. After stirring for 22 hours, the mixture was diluted with benzene (15 ml.) and filtered through a pad of Celite. The filtrate was poured into cold water and extracted with ethyl acetate (100 ml.). The extract was washed with water, a dilute aqueous solution of sodium bicarbonate, water and then an aqueous solution of sodium chloride successevely. Drying and removal of the solvent left an oil (3.40 g.), which was chromatographed on silica gel (60 g.) with a mixed solvent of methylene chloride and ethyl acetate (20:1 by volume) as an eluent to give benzyl 2-azido-2-[3-phenoxyacetamido-4-(2,2,2-trichloroethoxycarbonylthio)-2-oxo-1-azetidinyl]acetate (2.20 g.). Further, the same product (160 mg.) was recovered from the other fractions.

I.R. (CH$_2$Cl$_2$): 3395, 2120, 1790, 1750, 1725, 1695 cm$^{-1}$

Preparation 5

To benzyl 3-methyl-2-(3-phenoxyacetamido-4-mercapto-2-oxo-1-azetidinyl)-3-butenoate (2.945 g.) were added methylene chloride (25 ml.) and 2,2,2-trichloroethyl chloroformate (1.11 ml.) at −78° C. with stirring. To the resultant mixture was added dropwise pyridine (0.81 ml.) over a period of 5 minutes, and the mixture was allowed to warm to 0° C. over a period of 70 minutes and kept at 0° C. for 45 minutes with stirring. The reaction mixture was concentrated and the concentrate was partitioned between ethyl acetate and ice-water. The separated organic layer was washed successively with dilute hydrochloric acid, water, an aqueous solution of sodium bicarbonate and sodium chloride and a saturated aqueous solution of sodium chloride. Drying over magnesium sulfate and removal of the solvent left an oil (4.60 g.) of benzyl 3-methyl-2-[3-phenoxyacetamido-4-(2,2,2-trichloroethoxycarbonylthio)-2-oxo-1-azetidinyl]-3-butenoate.

I.R. (CH$_2$Cl$_2$): 3390, 1775, 1730, 1690 cm$^{-1}$

N.M.R. δppm (CDCl$_3$): 1.92 (3H, s), 4.65 (2H, s), 4.72 (2H, s), 4.8–5.2 (3H, m), 5.21 (2H, s), 5.47 (1H, d.d, J=8,4 Hz), 6.00 (1H, d, J=4 Hz), 6.8–7.6 (10H, m)

Preparation 6

A solution of benzyl 3-methyl-2-[3-phenoxyacetamido-4-(2,2,2-trichloroethoxycarbonylthio)-2-oxo-1-azetidinyl]-3-butenoate (4.60 g.) and triethylamine (1.13 ml.) in benzene (45 ml.) was stirred at room temperature for 1.5 hours. The reaction mixture was diluted with benzene (40 ml.), and washed successively with dilute hydrochloric acid, water and an aqueous solution of sodium chloride. Drying over magnesium sulfate and removal of the solvent left an oil (4.29 g.) of benzyl 3-methyl-2-[3-phenoxyacetamido-4-(2,2,2-trichloroethoxycarbonylthio)-2-oxo-1-azetidinyl]-2-butenoate.

I.R. (CH$_2$Cl$_2$): 3400, 1775, 1720, 1690 cm$^{-1}$

N.M.R. δppm (CDCl$_3$): 2.14 (3H, s), 2.28 (3H, s), 4.57 (2H, s), 4.77 (2H, s), 5.19 (1H, d.d, J=8, 5.5 Hz), 5.23 (2H, s), 5.96 (1H, d, J=5.5 Hz), 6.8–7.6 (10H, m)

Preparation 7

Into a solution of benzyl 3-methyl-2-[3-phenoxyacetamido-4-(2,2,2-trichloroethoxycarbonylthio)-2-oxo-1-azetidinyl]-2-butenoate (4.49 g.) in ethyl acetate (60 ml.) was bubbled a mixed gas of ozone and oxygen at −78° C. until a colar of ozone does not disappered. After the excess of ozone was removed from the reaction mixture by bubbling with a nitrogen gas, the solution was allowed to warm to −30° C. and poured into a solution of sodium bisulfite (10 g.) and sodium sulfite (6.3 g.) in water (100 ml.). The mixture was shaken and the separated organic layer was washed with a dilute aqueous solution of sodium chloride and a saturated aqueous solution of sodium chloride. Drying over magnesium sulfate and removal of the solvent left a crystalline residue. Addition of diethyl ether (20 ml.) and filtration afforded crystals (3.32 g.) of benzyl [3-phenoxyacetamido-4-(2,2,2-trichloroethoxycarbonylthio)-2-oxo-1-azetidinyl]glyoxylate, mp 152.0° C. (dec.).

I.R. (Nujol): 3330, 1820, 1735, 1710, 1660 cm$^{-1}$

N.M.R. δppm (DMSO-d$_6$): 4.68 (2H, s), 5.12 (2H, s), 5.36 (2H, s), 5.52 (1H, broad t, J=7 Hz), 6.15 (1H, d, J=6.5 Hz), 6.8–7.6 (10H, m), 9.15 (1H, d, J=7.5 Hz)

Preparation 8

To a solution of benzyl [3-phenoxyacetamido-4-(2,2,2-trichloroethoxycarbonylthio)-2-oxo-1-azetidinyl]glyoxylate (7.5 g.) and acetic acid (2.28 ml.) in tetrahydrofuran (30 ml.) was added portionwise sodium borohydride (480 mg.) over a period of half an hour at 0° C. After stirring for 10 minutes, the reaction mixture was diluted with methylene chloride (50 ml.), poured into a mixture of sodium bicarbonate (6.0 g.) in water (80 ml.) and a saturated aqueous solution of sodium chloride (20 ml.), and then extracted with methylene chloride (100 ml.). The extract was washed with a saturated aqueous solution of sodium chloride, dried over magnesium sulfate, and then filtered through a pad of Celite. Removal of the solvent gave an amorphous solid (7.60 g.) of benzyl 2-[3-phenoxyacetamido-4-(2,2,2-trichloroethoxycarbonylthio)-2-oxo-1-azetidinyl]-2-hydroxyacetate.

I.R. (CH$_2$Cl$_2$): 1785, 1735, 1720, 1695 cm$^{-1}$

Preparation 9

The same product (50 mg.) as that of Preparation 8 was obtained by reducing the same starting compound (500 mg.) as that of Preparation 8 with sodium cyanoborohydride (80 mg.) in substantially the same manner as that of Preparation 8.

Preparation 10

To a solution of benzyl 2-[3-phenoxyacetamido-4-(2,2,2-trichloroethoxycarbonylthio)-2-oxo-1-azetidinyl]-2-hydroxyacetate (3.8 g.) in methylene chloride (25 ml.) were added 2,6-lutidine (1.12 ml.) and thionyl chloride (0.70 ml.) at −35° C. The mixture was allowed to warm to 0° C. over a period of 30 minutes and stirred for 30 minutes at the same temperature. The reaction mixture was diluted with methylene chloride, washed twice with ice-water and an aqueous solution of sodium chloride, and dried over magnesium sulfate. Filtration and removal of the solvent left an amorphous solid (3.80 g.) of benzyl 2-[3-phenoxyacetamido-4-(2,2,2-trichloroethoxycarbonylthio)-2-oxo-1-azetidinyl]-2-chloroacetate.

I.R. (CH$_2$Cl$_2$): 1795, 1750, 1720, 1695 cm$^{-1}$

Preparation 11

To a solution of benzyl 2-[3-phenoxyacetamido-4-(2,2,2-trichloroethoxycarbonylthio)-2-oxo-1-azetidinyl]-2-chloroacetate (3.60 g.) in N,N-dimethylformamide (6 ml.) was added sodium azide (384 mg.) at 0° C., and the mixture was stirred at 0° C. for 50 minutes. The reaction mixture was poured into ice-water and extracted with ethyl acetate. The extract was washed twice with water and an aqueous solution of sodium chloride, dried over magnesium sulfate, and then evaporated to leave an oil (3.60 g.), which was chromatographed on silica gel (36 g.) with chloroform as an eluent to give an oil (1.71 g.) of benzyl 2-[3-phenoxyacetamido-4-(2,2,2-trichloroethoxy-carbonylthio)-2-oxo-1-azetidinyl]-2-azidoacetate.

I.R. (CH$_2$Cl$_2$): 2120, 1790, 1750, 1720, 1695 cm$^{-1}$

N.M.R. δppm (CDCl$_3$): 4.53 (2H, s), 4.72 (2H, s), 5.2–5.9 (5H, m), 6.8–7.6 (10H, m)

Preparation 12

A mixture of benzyl 2-[3-phenoxyacetamido-4-(2,2,2-trichloroethoxycarbonylthio)-2-oxo-1-azetidinyl]-2-azidoacetate (2.856 g.) and 10% palladium on carbon (600 mg.) in formic acid (27 ml.) was stirred at room temperature under hydrogen atmosphere. After stirring for an hour, to the mixture was added 5% palladium on carbon (600 mg.) in formic acid (8 ml.) and stirred under hydrogen atmosphere for additional 2.5 hours. The resultant mixture was filtered through a pad of Celite and the filter cake was washed with methylene chloride. The filtrate and washings were combined and concentrated in vacuo to a volume of 15 ml. A part of this concentrate was evaporated to dryness to give benzyl 2-[3-phenoxyacetamido-4-(2,2,2-trichloroethoxycarbonylthio)-2-oxo-1-azetidinyl]-2-aminoacetate.

I.R. (CH$_2$Cl$_2$): 3450 (shoulder), 3400, 1780, 1740, 1720, 1695 cm$^{-1}$

The above concentrate was cooled to 0° C., and an acetic formic anhydride (15 ml.) solution, which was prepared by two parts of acetic anhydride and one part of formic acid, was added thereto. The resultant mixture was stirred at 0° C. for an hour and evaporated to dryness in vacuo. The residue was dissolved in ethyl acetate, and washed with a chilled dilute aqueous solution of sodium bicarbonate and an aqueous solution of sodium chloride. Drying over magnesium sulfate and removal of the solvent left an oil (2.75 g.), which was chromatographed on silica gel (30 g.) with methylene chloride and a mixture of methylene chloride and ethyl acetate to give an amorphous solid (2.19 g.) of benzyl 2-[3-phenoxyacetamido-4-(2,2,2-trichloroethoxycarbonylthio)-2-oxo-1-azetidinyl]-2-formamidoacetate.

I.R. (CH$_2$Cl$_2$): 3390, 1785, 1745, 1720 (shoulder), 1700 (shoulder), 1695 cm$^{-1}$

| N.M.R. δ ppm (CDCl$_3$): | 4.56 (2H, s), |
|---|---|
| | 4.71 (s) ⎫ |
| | 4.80 (broad s) ⎬ (2H), |
| | 5.26 (s) ⎫ |
| | 5.30 (s) ⎬ (2H), |
| | 5.4–5.9 (2H, m), |
| | 6.00 (d, J = 8Hz) ⎫ |
| | 6.13 (d, J = 8Hz) ⎬ (1H), |
| | 6.8–7.8 (10, m), |
| | 8.22 (s) ⎫ |
| | 8.27 (s) ⎬ (1H) |

Preparation 13

To a solution of benzyl 2-[3-phenoxyacetamido-4-(2,2,2-trichloroethoxycarbonylthio)-2-oxo-1-azetidinyl]-2-formamidoacetate (2.70 g.) and 2,6-lutidine (11.4 ml.) in methylene chloride (16 ml.) was added dropwise phosphorus oxychloride (1.12 ml.) at 0° C. After stirring at the same temperature for 4.8 hours, the mixture was diluted with a mixture of benzene and ethyl acetate (120 ml.) (6:4 by volume), and washed successively with a chilled dilute aqueous solution of sodium chloride, a mixture of 10% phosphoric acid (75 ml.) and a saturated aqueous solution of sodium chloride, a dilute aqueous solution of sodium chloride, ice-water and a saturated aqueous solution of sodium chloride. Drying over magnesium sulfate and removal of the solvent left an oil (2.5 g.), which was chromatographed on silica gel (30 g.) with a mixed solvent of benzene and ethyl acetate (5:1 by volume) as an eluent to give an amorphous solid of benzyl 2-[3-phenoxyacetamido-4-(2,2,2-trichloroethoxycarbonylthio)-2-oxo-1-azetidinyl]-2-isocyanoacetate.

I.R. (CH$_2$Cl$_2$): 3390, 2140, 1795, 1760, 1720, 1695 cm$^{-1}$

| N.M.R. δ ppm (acetone-d$_6$): | 4.64 (2H, s), |
|---|---|
| | 4.96 (2H, s), |
| | 5.26 (AB$_q$) ⎫ |
| | 5.34 (AB$_q$) ⎬ (2H), |
| | 5.59 (d,d, J = 5, 8Hz) ⎫ |
| | 5.65 (d,d, J = 5, 8Hz) ⎬ (1H), |
| | 5.98 (d, J = 5Hz) ⎫ |
| | 6.02 (d, J = 5Hz) ⎬ (1H), |
| | 6.26 (s) ⎫ |
| | 6.37 (s) ⎬ (1H), |
| | 6.8–7.6 (10H, m), |
| | 8.59 (1H, d, J = 8Hz) |

Preparation 14

The same product (33 mg.) as that of Preparation 13 was obtained by reacting the same starting compound (100 mg.) as that of Preparation 13 with phosphorus oxychloride (30 μl) in the presence of pyridine (0.2 ml.) instead of 2,6-lutidine in substantially the same manner as that of Preparation 13.

What is claimed is:

1. A compound of the formula:

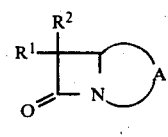

in which

R$^1$ is amino, acylamino, mono- or di- or triphenyl (lower) alkylamino,

R$^2$ is hydrogen or lower alkoxy,

A is a group of the formula:

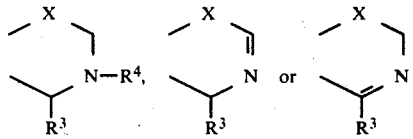

wherein

X is —S— or

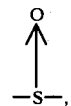

R$^3$ is carboxy or a protected carboxy group and

R$^4$ is hydrogen, hydroxy or acyl, and pharmaceutically acceptable salts thereof.

2. The compound of claim 1, in which

R$^1$ is amino, acylamino, mono- or di- or tri-phenyl (lower) alkylamino,

R$^2$ is hydrogen or lower alkoxy,

R³ is carboxy or an esterified carboxy group and
R⁴ is hydrogen, hydroxy or acyl.

3. The compound of claim 2, in which
R¹ is amino, phenoxy (lower) alkanoylamino, or thienyl (lower) alkanoylamino,
R² is hydrogen or lower alkoxy,
R³ is carboxy, phenyl (lower) alkoxycarbonyl, nitrophenyl (lower) alkoxycarbonyl, lower alkoxy (lower) alkoxycarbonyl, or lower alkanoyloxy (lower) alkoxycarbonyl, and
R⁴ is hydrogen, hydroxy, lower alkanoyl or trihalo (lower) alkanesulfonyl.

4. The compound of claim 3, in which
R¹ is amino, phenoxy(lower)alkanoylamino or thienyl(lower)alkanoylamino and
A is a group of the formula:

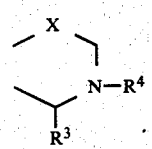

wherein X, R³ and R⁴ are each as defined in claim 3.

5. The compound of claim 4, which is 7-phenoxyacetamido-8-oxo-3-hydroxy-5-thia-1,3-diazabicyclo[4,2,0]octane-2-carboxylic acid.

6. The compound of claim 4, which is benzyl 7-amino-8-oxo-3-trifluoromethanesulfonyl-5-thia-1,3-diazabicyclo[4,2,0]octane-2-carboxylate tosylate.

7. The compound of claim 3, in which
R¹ is phenoxy(lower)alkanoylamino,
R² is hydrogen, and
A is a group of the formula:

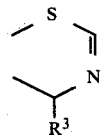

wherein R³ is carboxy or phenyl(lower)alkoxycarbonyl.

8. The compound of claim 7, which is 7-phenoxyacetamido-8-oxo-5-thia-1,3-diazabicyclo[4,2,0]oct-3-ene-2-carboxylic acid.

9. The compound of claim 3, in which
R¹ is phenoxy(lower)alkanoylamino or thienyl(lower)alkanoylamino,
R² is hydrogen, and
A is a group of the formula:

wherein X and R³ are each as defined in claim 3.

10. The compound of claim 9, which is pivaloyloxymethyl 7-phenoxyacetamido-8-oxo-5-thia-1,3-diazabicyclo[4,2,0]oct-2-ene-2-carboxylate.

11. A antimicrobial composition comprising a compound of claim 1, as an active ingredient, in association with non-toxic, pharmaceutically acceptable carrier or excipient.

12. A method for treating an infectious diseases caused by pathogenic microorganisms, which comprises administering an antimicrobially effective amount of a compound of claim 1 to infected human being and animals.

* * * * *